United States Patent
Yardi et al.

(10) Patent No.: US 11,172,908 B2
(45) Date of Patent: Nov. 16, 2021

(54) METHOD AND SYSTEMS FOR CORRECTING X-RAY DETECTOR TILT IN X-RAY IMAGING

(71) Applicant: GE Precision Healthcare LLC, Milwaukee, WI (US)

(72) Inventors: Vinayak Yardi, Bangalore (IN); Prabhu Rajasekaran, Bangalore (IN); Nasir Ahmed Desai, Bangalore (IN); Ashwini Chikkanayakanahalli Vasudeva, Bangalore (IN)

(73) Assignee: GE Precision Healthcare LLC, Milwaukee, WI (US)

( * ) Notice: Subject to any disclaimer, the term of this patent is extended or adjusted under 35 U.S.C. 154(b) by 6 days.

(21) Appl. No.: 16/526,911

(22) Filed: Jul. 30, 2019

(65) Prior Publication Data
US 2021/0030389 A1 Feb. 4, 2021

(51) Int. Cl.
*A61B 6/00* (2006.01)
*A61B 8/08* (2006.01)
(Continued)

(52) U.S. Cl.
CPC ............ *A61B 6/587* (2013.01); *A61B 6/40* (2013.01); *A61B 6/42* (2013.01); *A61B 6/4208* (2013.01); *A61B 6/4233* (2013.01); *A61B 6/4283* (2013.01); *A61B 6/4291* (2013.01); *A61B 6/44* (2013.01); *A61B 6/4405* (2013.01); *A61B 6/4452* (2013.01); *A61B 6/46* (2013.01);
(Continued)

(58) Field of Classification Search
CPC .......... A61B 6/40; A61B 6/42; A61B 6/4208; A61B 6/4233; A61B 6/4283; A61B 6/4291; A61B 6/44; A61B 6/4405; A61B 6/4429; A61B 6/46; A61B 6/461; A61B 6/462; A61B 6/467; A61B 6/469; A61B 6/52; A61B 6/5205; A61B 6/5211; A61B 6/54; A61B 6/542; A61B 6/545; A61B 6/547; A61B 6/58; A61B 6/582; A61B 6/583; A61B 6/584; A61B 6/585; A61B 6/587; A61B 6/588
USPC ................... 378/189, 196–198, 205, 207, 62
See application file for complete search history.

(56) References Cited

U.S. PATENT DOCUMENTS

| 5,359,637 | A | * | 10/1994 | Webber | .................. | A61B 6/025 |
| | | | | | | 378/162 |
| 6,081,577 | A | * | 6/2000 | Webber | ................ | G01N 23/046 |
| | | | | | | 378/23 |

(Continued)

FOREIGN PATENT DOCUMENTS

WO  2018183160 A1  10/2018

OTHER PUBLICATIONS

European application No. 20187281.9 filed Jul. 22, 2020—European extended Search Report dated Dec. 7, 2020; 7 pages.

*Primary Examiner* — Allen C. Ho
(74) *Attorney, Agent, or Firm* — McCoy Russell LLP

(57) ABSTRACT

Various methods and systems are provided for x-ray imaging. In one embodiment, a method comprises acquiring, with an x-ray detector tilted at an angle with respect to an x-ray source, an x-ray image, calculating the angle from the x-ray image, generating a corrected x-ray image based on the calculated angle, and displaying the corrected x-ray image. In this way, tilt artifacts caused by the x-ray detector being tilted with respect to the x-ray source may be removed from an x-ray image.

20 Claims, 10 Drawing Sheets

(51) Int. Cl.
*G06T 3/00* (2006.01)
*G06T 7/00* (2017.01)
*G06T 11/00* (2006.01)

(52) U.S. Cl.
CPC .............. *A61B 6/461* (2013.01); *A61B 6/462* (2013.01); *A61B 6/467* (2013.01); *A61B 6/469* (2013.01); *A61B 6/52* (2013.01); *A61B 6/5205* (2013.01); *A61B 6/5211* (2013.01); *A61B 6/54* (2013.01); *A61B 6/542* (2013.01); *A61B 6/545* (2013.01); *A61B 6/547* (2013.01); *A61B 6/58* (2013.01); *A61B 6/582* (2013.01); *A61B 6/583* (2013.01); *A61B 6/584* (2013.01); *A61B 6/585* (2013.01); *A61B 6/588* (2013.01); *A61B 8/5223* (2013.01); *A61B 6/4429* (2013.01); *G06T 3/00* (2013.01); *G06T 7/0012* (2013.01); *G06T 11/005* (2013.01)

(56) References Cited

U.S. PATENT DOCUMENTS

| | | | | |
|---|---|---|---|---|
| 6,354,737 | B1 * | 3/2002 | Hufe | H04N 5/32 |
| | | | | 378/205 |
| 6,890,098 | B2 * | 5/2005 | Rosner | G01N 23/04 |
| | | | | 378/196 |
| 6,890,099 | B2 * | 5/2005 | Tanaka | A61B 6/08 |
| | | | | 378/197 |
| 7,003,145 | B2 * | 2/2006 | Polkus | A61B 6/08 |
| | | | | 378/145 |
| 7,156,553 | B2 | 1/2007 | Hiroshi | |
| 7,311,440 | B2 * | 12/2007 | Yoon | A61B 6/145 |
| | | | | 250/370.09 |
| 7,628,537 | B2 * | 12/2009 | Schulze-Ganzlin | A61B 6/145 |
| | | | | 378/170 |
| 7,775,713 | B2 * | 8/2010 | Klemola | A61B 6/145 |
| | | | | 378/191 |
| 7,778,392 | B1 * | 8/2010 | Berman | A61B 6/032 |
| | | | | 378/210 |
| 7,780,350 | B2 * | 8/2010 | Tranchant | G05B 19/401 |
| | | | | 378/205 |
| 7,806,589 | B2 * | 10/2010 | Tashman | A61B 6/505 |
| | | | | 378/197 |
| 8,126,111 | B2 * | 2/2012 | Uhde | A61B 6/547 |
| | | | | 378/41 |
| 8,275,187 | B2 * | 9/2012 | Oogami | A61B 6/06 |
| | | | | 382/131 |
| 8,300,764 | B2 * | 10/2012 | Yamaguchi | G06T 7/73 |
| | | | | 378/62 |
| 8,344,327 | B2 * | 1/2013 | Yamaguchi | A61B 6/5241 |
| | | | | 250/363.07 |
| 8,670,521 | B2 * | 3/2014 | Bothorel | A61B 6/14 |
| | | | | 378/39 |
| 9,429,665 | B2 * | 8/2016 | Jobst | A61B 6/027 |
| 9,541,509 | B2 * | 1/2017 | Akahori | A61B 6/486 |
| 10,076,302 | B2 * | 9/2018 | Franklin | G21K 1/02 |
| 10,531,845 | B2 * | 1/2020 | Rajasekaran | A61B 6/4233 |
| 10,758,204 | B2 * | 9/2020 | Grondin | A61B 6/4035 |
| 10,779,791 | B2 * | 9/2020 | Tkaczyk | A61B 6/4405 |
| 2019/0099151 | A1 | 4/2019 | Rajasekaran et al. | |

* cited by examiner

METHOD AND SYSTEMS FOR CORRECTING X-RAY DETECTOR TILT IN X-RAY IMAGING

FIELD

Embodiments of the subject matter disclosed herein relate to x-ray imaging.

BACKGROUND

Imaging technologies such as x-ray imaging allow for non-invasive acquisition of images of internal structures or features of a subject or an object. Digital x-ray imaging systems produce digital data which can be reconstructed into radiographic images. In digital x-ray imaging systems, radiation from a source is directed toward the subject in a medical application, a package or baggage in a security screening application, or a fabricated component in an industrial quality control inspection application. A portion of the radiation passes through the subject/object and impacts a detector. The detector includes an array of discrete picture elements or detector pixels and generates output signals based upon the quantity or intensity of the radiation impacting each pixel region. The output signals are subsequently processed to generate an image that may be displayed for review. These images are used to identify and/or examine the internal structures and organs within a patient's body, objects within a package or container, or defects such as cracks within a fabricated component.

BRIEF DESCRIPTION

In one embodiment, a method comprises acquiring, with an x-ray detector tilted at an angle with respect to an x-ray source, an x-ray image, calculating the angle from the x-ray image, generating a corrected x-ray image based on the calculated angle, and displaying the corrected x-ray image. In this way, tilt artifacts caused by the x-ray detector being inadvertently tilted with respect to the x-ray source may be reduced or removed altogether from an x-ray image.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 2:
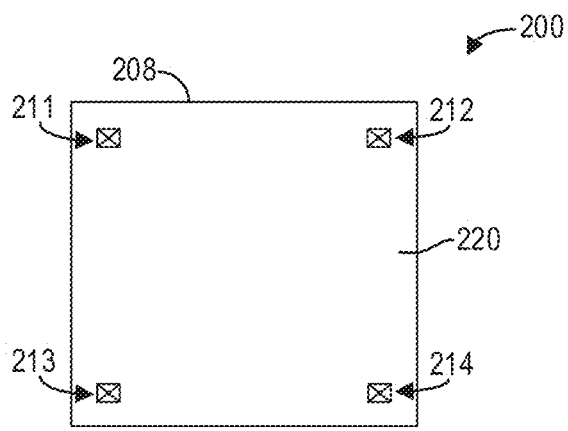
FIG. 2 shows a diagram illustrating an example x-ray detector configured with markers for detecting tilt according to an embodiment.
Figure 3:
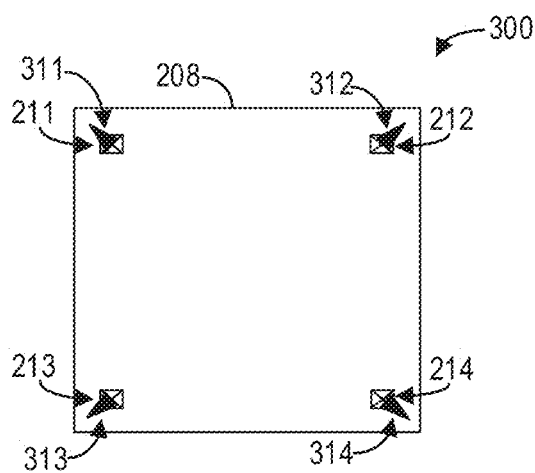
FIG. 3 shows a diagram illustrating the example x-ray detector of FIG. 2 with shadows of the markers resulting from no detector tilt according to an embodiment.
Figure 4:
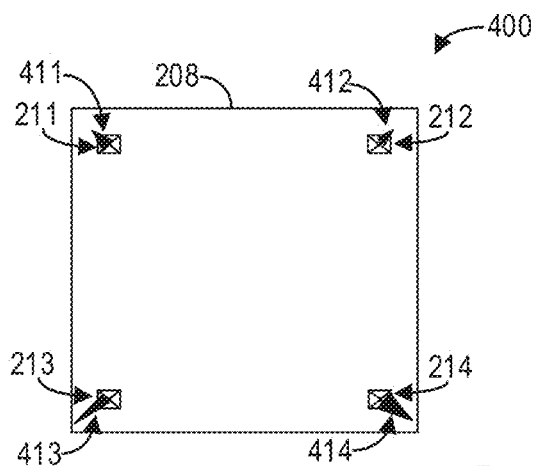
FIG. 4 shows a diagram illustrating the example x-ray detector of FIG. 2 with shadows of the markers resulting from vertical tilt according to an embodiment.
Figure 10:
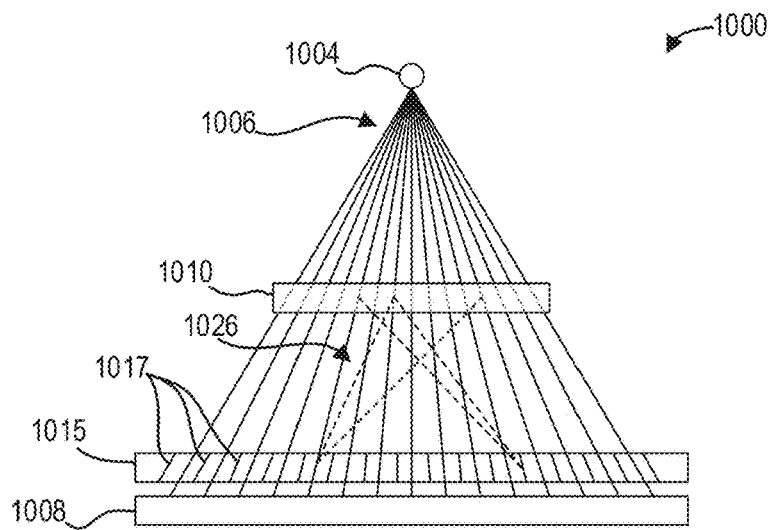
FIG. 10 shows a diagram illustrating an example position of an anti-scatter grid relative to an x-ray source, an x-ray detector, and a subject being imaged according to an embodiment.
Figure 11:
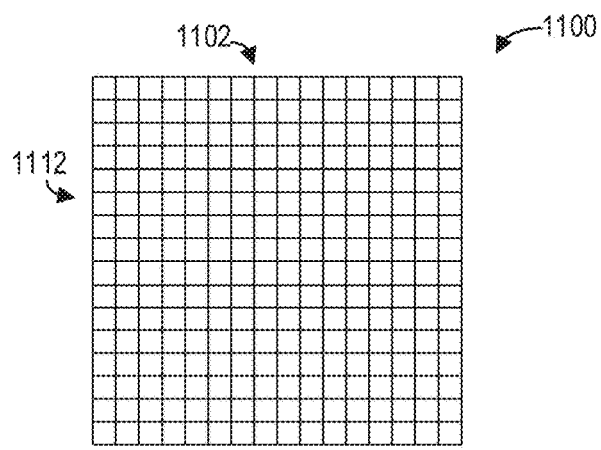
FIG. 11 shows a diagram illustrating an example grid pattern formed by an anti-scatter grid in the absence of detector tilt according to an embodiment.
Figure 12:
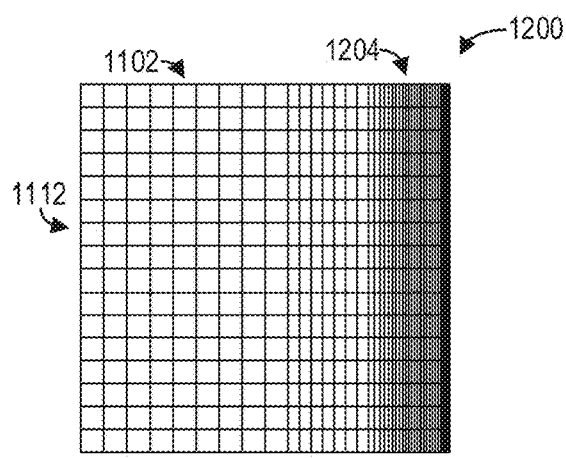
FIG. 12 shows a diagram illustrating an example grid pattern formed by an anti-scatter grid in the presence of lateral detector tilt according to an embodiment.

The following description relates to various embodiments of x-ray imaging. In particular, systems and methods for correcting detector tilt in mobile x-ray imaging are provided. A mobile x-ray imaging system, such as the mobile x-ray imaging system depicted in FIG. 1, includes an x-ray detector which may be manually positioned relative to an x-ray source. In mobile x-ray imaging systems, placement of the x-ray detector depends on many factors such as mobility constraints of the subject and other space constraints. Images that are generated using data acquired with detector placement with such constraints disadvantageously result in tilt artifacts. These tilt artifacts adversely affect diagnosis and may result in the need for additional scans, thereby increasing associated costs and time. In the case of medical applications, the additional scans also result in an increase in radiation exposure and inconvenience to the subject. One approach to detecting and correcting detector tilt in x-ray imaging data includes configuring an x-ray detector with radiation blocking markers on the surface of the x-ray detector, as depicted in FIG. 2, which cast shadows on the x-ray detector, as depicted in FIGS. 3 and 4. A tilting of the x-ray detector relative to the x-ray source thus results in different shapes of the shadows. As the geometry of the markers relative to the x-ray detector are known, as depicted in FIGS. 5-8, the shadows of the markers in an image may be analyzed to determine the amount of detector tilt. Thus, a method for correcting detector tilt, such as the method depicted in FIG. 9, includes analyzing shadows from markers in an x-ray image, and generating a corrected x-ray image based on the analysis of the shadows. Another approach to detecting and correcting detector tilt in x-ray imaging data includes using an anti-scatter grid, as depicted in FIG. 10, for preventing scatter radiation from being detected by the x-ray detector. The anti-scatter grid also creates a shadow in the x-ray image, which may correspond to a grid pattern as shown in FIG. 11 in the absence of detector tilt. If the x-ray detector is tilted, however, the grid pattern may be warped in the x-ray image, as depicted in FIG. 12. A method for detecting detector tilt and correcting x-ray image data, such as the method depicted in FIG. 13, therefore may include analyzing the grid pattern in an x-ray image created by an anti-scatter grid to determine an amount of detector tilt. Further, a person reviewing an x-ray image may notice that the x-ray image includes tilt artifacts. A graphical user interface, such as the graphical user interfaces depicted in FIGS. 14 and 15, allow a user to virtually tilt the x-ray detector to apply tilt corrections to the x-ray image. A workflow for applying user corrections to an x-ray image, such as the method depicted in FIG. 16, includes receiving user input regarding an amount of tilt to apply to an image and updating or correcting the x-ray image according to the amount of tilt input by the user.

Figure 1:
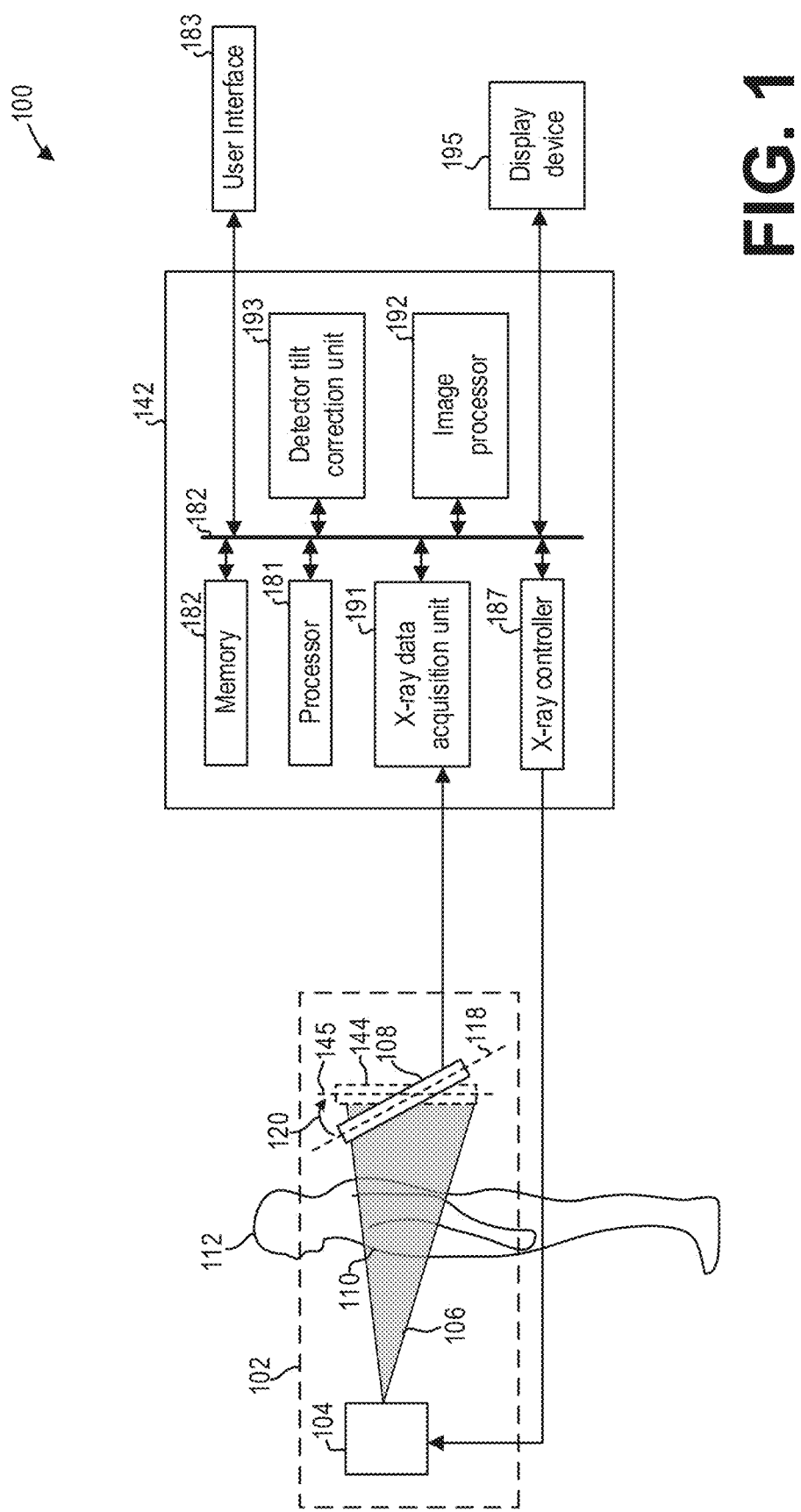
FIG. 1 shows an example mobile x-ray imaging system according to an embodiment.

Turning now to FIG. 1, a block diagram of an x-ray imaging system 100 in accordance with an embodiment is shown. The x-ray imaging system 100 includes an image acquisition unit 102 and an operating console 142. The operating console 142 includes a processor 181, a memory 182, an x-ray controller 187, an x-ray data acquisition unit 191, an image processor 192, and a detector tilt correction unit 193. The operating console 142 is communicatively coupled to a user interface 183 and a display device 195, as depicted, though it should be appreciated that in some examples the operating console 142 may further comprise one or more of the user interface 183 and the display device 195. In some examples, the x-ray imaging system 100 comprises a mobile x-ray imaging system, such that the image acquisition unit 102 and the operating console 142 are portable or mobile.

The image acquisition unit 102 includes a radiation source such as an x-ray source 104. The x-ray source 104 is configured to emit a radiation beam such as an x-ray beam 106 having a field-of-view towards an object 110. In the example of FIG. 1, the object 110 is an anatomical region or a region of interest in a subject such as a patient 112. In another example, the object 110 may correspond to a package or a baggage in a security screening application. In yet another example, the object 110 may be a fabricated component in an industrial application.

In some examples, the x-ray imaging system 100 further includes a patient table (not shown) configured to support the patient 112. The x-ray beam 106 upon impinging on the anatomical region 110 may be attenuated differently by portions of the anatomical region 110. An x-ray detector 108 that is disposed in the field-of-view of the x-ray beam 106 acquires the attenuated x-ray beam. The x-ray detector 108 may comprise, as non-limiting examples, an x-ray exposure monitor, an electric substrate, and so on. The x-ray detector 108 is moveable by an operator of the mobile x-ray imaging system 100 for manually positioning relative to the x-ray beam 106.

The operating console 142 comprises a processor 181, a memory 182, an x-ray controller 187, an x-ray data acquisition unit 191, an image processor 192, and a detector tilt correction unit 193. X-ray image data acquired by the x-ray detector 108 is transmitted from the x-ray detector 108 and is received by the x-ray data acquisition unit 191. The collected x-ray image data are image-processed by the image processor 192. A display device 195 communicatively coupled to the operating console 142 displays an image-processed x-ray image thereon. The x-ray controller 187 supplies power of a suitable voltage current to the x-ray source 104 for powering the x-ray source 104.

The image acquisition unit 102 is further configured to generate an x-ray image corresponding to the object 110 based on the detected x-ray beam. In the example of FIG. 1, the x-ray image is a projection of the anatomical region 110 of the subject 112 in a detector plane 118. The x-ray image includes a plurality of image pixels corresponding to a plurality of image pixel positions in the detector plane 118.

Any misalignment between the detector plane 118 and the object 110 results in tilt image artifacts in the resulting x-ray image. As discussed further herein, the detector tilt correction unit 193 is configured to detect and correct any tilt image artifacts in the x-ray image to generate a corrected x-ray image. To that end, the detector tilt correction unit 193 is configured to receive the x-ray image acquired by the image acquisition unit 102. Additionally, the detector tilt correction unit 193 is also configured to receive a tilt parameter corresponding to the detector plane 118. In one embodiment, the tilt parameter is obtained from a user interface 183. In another embodiment, the tilt parameter may be generated by automatic processing of a reference image stored in the memory 182.

The detector tilt correction unit 193 is configured to generate a corrected x-ray image based on the x-ray image and the tilt parameter. The corrected x-ray image corresponds to a projection of the anatomical region 110 of the subject 112 in a corrected detector plane 145. The corrected x-ray image includes a plurality of corrected pixels corresponding to a plurality of corrected pixel positions in a corrected detector position 144 aligned with the corrected detector plane 145. The tilt parameter may comprise one or more tilt angles 120 which describe an angular distance from the detector plane 118 of the x-ray detector 108 to the corrected detector plane 145. The one or more tilt angles 120 may comprise one or more of a horizontal tilt angle and a vertical tilt angle, wherein the horizontal tilt angle indicates a tilt or rotation around a horizontal axis (e.g., pitch) while the vertical tilt angle indicates a tilt or rotation around a vertical axis (e.g., yaw). In some examples, the one or more tilt angles 120 further comprises a rotation angle of the x-ray detector 108 around a center point of the x-ray detector (e.g., roll).

Further, the detector tilt correction unit 193 is also configured to receive one or more imaging parameters from one or more of the image acquisition unit 102 and the user interface 183. The one or more imaging parameters may include a first field-of-view angle, a second field-of-view angle, source coordinates representative of a position of the x-ray source 104, detector coordinates representative of a position of the x-ray detector 108, and combinations thereof. In some examples, the detector tilt correction unit 193 is configured to generate a corrected x-ray image based on the x-ray image, the tilt parameter, and one or more of the imaging parameters.

In order to generate the corrected x-ray image from the x-ray image, the detector tilt correction unit 193 is configured to determine a perspective projection of the detector plane 118 in the field of view of the x-ray beam 106 to determine a projection plane. The detector plane 118 includes a plurality of image pixels that correspond to a plurality of image pixel positions in the detector plane 118. Further, the detector tilt correction unit 193 is configured to rotate the projection plane to the corrected detector plane 145 using a rotation matrix. The corrected detector plane 145 includes a plurality of rotated pixel positions. The detector tilt correction unit 193 is configured to assign the plurality of image pixel values to a plurality of rotated pixel values in the corrected detector plane 145. The plurality of rotated pixels correspond to the plurality of rotated pixel positions. Moreover, the detector tilt correction unit 193 is configured to interpolate the plurality of rotated pixels to generate the plurality of corrected pixels. The plurality of rotated pixel positions may also be interpolated to generate the plurality of corrected pixel positions.

It should be appreciated that the projection plane is rotatable in a three-dimensional space with reference to a pivot axis or tilt axis. The pivot axis or tilt axis includes a first tilt axis parallel to an x-axis of a Cartesian coordinate system, a second tilt axis parallel to a y-axis of the Cartesian coordinate system, and a third tilt axis parallel to a z-axis of the Cartesian coordinate system, such that the x-axis, y-axis, and z-axis relate to the pitch, yaw, and roll of the x-ray detector 108 as described hereinabove. The tilt parameter thus includes at least one of a first tilt angle corresponding to the first tilt axis (e.g., the horizontal tilt angle), a second tilt angle corresponding to the second tilt axis (e.g., the vertical tilt angle), and a third tilt angle corresponding to the third tilt axis (e.g., the rotation angle). In some examples, the x-ray image is transformed by rotating the x-ray image along the first tilt axis by the first tilt angle. In other examples, the x-ray image is transformed by rotating the x-ray image along the second tilt axis by the second tilt angle. In further examples, the x-ray image is transformed by rotating the x-ray image along the third tilt axis by the third tilt angle. In general, the x-ray image may be transformed by rotating the x-ray image along at least one of the first tilt axis, the second tilt axis, and the third tilt axis.

In some examples, the detector tilt correction unit 193 is configured to determine the projection plane by determining homogenous coordinates for each image pixel in the x-ray image based on the one or more imaging parameters. Specifically, the detector plane 118 is placed in a projection space determined by the field of view of the x-ray beam 106 using a perspective projection technique. Additionally, use of the perspective projection technique entails adjusting the position of the detector plane 118 in the projection space by shifting along one or more coordinate axes. The shifting of the detector plane 118 in the projection space includes adjusting the detector plane dimensions to match dimensions of a projection frustum formed by the x-ray beam 106 in the projection space. In one example, the perspective projection of the detector plane 118 to the projection plane is performed via a projection matrix.

Each image pixel position corresponding to the detector plane 118 includes a first x-coordinate value, a first y-coordinate value, and a first z-coordinate value. The first x-coordinate value, the first y-coordinate value, and the first z-coordinate value are representative of coordinates in the Cartesian coordinate system. Furthermore, the first x-coordinate value, the first y-coordinate value, and the first z-coordinate value are respectively measured along the x-axis, y-axis, and z-axis of the Cartesian coordinate system, wherein the x-ray source 104 is positioned at the origin of the Cartesian coordinate system and the center of the x-ray detector 108 is aligned with the x-ray source 104 along the z-axis.

In one example, the use of the perspective projection technique includes providing a first w-coordinate with each of the plurality of image pixel positions in the detector plane 118. For example, each w-coordinate may have a value of one. It may be noted that the first w-coordinate is measured along a w-axis, wherein the x-axis, the y-axis, the z-axis, and the w-axis form a four-dimensional homogenous coordinate system. In the four-dimensional coordinate system, the first tilt axis coincides with the x-axis, the second tilt axis coincides with the y-axis, and the third tilt axis coincides with the z-axis.

Moreover, the perspective projection further includes adjusting the values of the first x-coordinate value, the first y-coordinate value, the first z-coordinate value, and the first w-coordinate value via use of the projection matrix. In one example, the perspective projection of an image pixel position is given by:

$$\begin{bmatrix} x_m \\ y_m \\ z_m \\ w_m \end{bmatrix} = \begin{bmatrix} \frac{2n}{r-l} & 0 & \frac{l+r}{l-r} & 0 \\ 0 & \frac{2n}{t-b} & \frac{b+t}{t-b} & 0 \\ 0 & 0 & \frac{-f-n}{f-n} & \frac{-2fn}{f-n} \\ 0 & 0 & -1 & 0 \end{bmatrix} \begin{bmatrix} x_1 \\ y_1 \\ z_1 \\ w_1 \end{bmatrix},$$

wherein the vector $[x_1, y_1, z_1, w_1]$ is representative of homogenous coordinates of an image pixel position in the detector plane 118, the vector $[x_m, y_m, z_m, w_m]$ is representative of modified homogenous coordinates of a projected pixel position, n is a near plane z value, f is a far plane z value, l is a near plane left side value, r is a near plane right side value, t is a near plane top side value, and b is a near plane bottom side value.

Further, processing the homogenous coordinates of a projected pixel includes moving the detector plane 118 in the projection space along the z-axis to adjust the dimensions of the x-ray image to match the dimensions of the frustum of the field of view of the x-ray beam 106. A modified first z-coordinate $z_m$ is determined based on the movement of the detector plane 118 along the z-axis. Further, processing the homoegenous coordinates includes modifying the first x-coordinate based on the first z-coordinate, the modified first z-coordinate, and the first x-coordinate values. The modified first x-coordinate value is given by, for example:

$$x_m = \frac{z_m}{z_1} x_1,$$

where $x_m$ is the modified x-coordinate value.

The first y-coordinate value is also modified similarly based on the first y-coordinate, the first z-coordinate, and the modified z-coordinate. The modified first y-coordinate value is given by:

$$y_m = \frac{z_m}{z_1} y_1,$$

where $y_m$ is the modified y-coordinate value.

It should be noted that, as depicted in the expressions above for $x_m$ and $y_m$, in some examples, a ratio of the modified z-coordinate and the first z-coordinate is used to determine the modified x-coordinate and the modified y-coordinate. In particular, the x-coordinate and the y-coordinate are respectively multiplied by the ratio of the modified z-coordinate and the first z-coordinate to obtain the modified x-coordinate and the modified y-coordinate respectively.

Similarly, modified homogenous coordinates of a plurality of projected pixel positions corresponding to the detector plane 118 are determined. In one embodiment, each of the modified homogenous coordinates may be scaled by the corresponding first modified w-coordinate to represent the projected pixel position in the Cartesian coordinate system.

Further, the detector tilt correction unit 193 is also configured to determine the plurality of rotated pixel positions corresponding to the corrected detector plane 145. In one embodiment, the projection plane or at least the detector plane 118 is rotated or tilted by at least one of a first tilt angle with respect to the x-axis, a second tilt angle with respect to the y-axis, and a third tilt angle with respect to the z-axis to determine the corrected detector plane 145. Specifically, the plurality of projected pixel positions is multiplied by the rotation matrix to obtain the plurality of rotated pixel positions. Each rotated pixel position among the plurality of rotated pixel positions includes a second x-coordinate value, a second y-coordinate value, and a second z-coordinate value.

In one example, the projection plane is tilted with respect to only the z-axis to determine the corrected detector plane 145. In this example, the tilt parameter includes a tilt angle that is representative of an angle between the detector plane 118 and the corrected detector plane 145.

As noted hereinabove, the detector tilt correction unit 193 is configured to determine a rotated pixel position by rotating the projected pixel positions via use of a rotation matrix. In one example, when the projection plane is rotated with respect to the x-axis, the rotation matrix may be represented as:

$$R_x = \begin{bmatrix} 1 & 0 & 0 \\ 0 & \cos\theta & -\sin\theta \\ 0 & \sin\theta & \cos\theta \end{bmatrix},$$

where θ is the first tilt angle.

The rotation matrix $R_x$ provided hereinabove is used to transform a projected pixel position to a corresponding rotated pixel position. As previously noted, each of the plurality of projected pixel positions includes a modified first x-coordinate, a modified first y-coordinate, and a modified first z-coordinate. A column vector having the modified first x-coordinate, the modified first y-coordinate, and the modified first z-coordinate is pre-multiplied by the rotation matrix $R_x$ to compute a column vector having the second x-coordinate, the second y-coordinate, and the second z-coordinate. In other embodiments, the rotation matrix R may be representative of a combined rotation of the projection plane with reference to two or more of the x-axis, the y-axis, and the z-axis.

Subsequent to the determination of the plurality of rotated pixel positions, image pixels of the corrected x-ray image may be determined by the detector tilt correction unit 193. In one example, pixel values corresponding to the image pixel positions of the detector plane 118 are assigned as pixel values to the corresponding rotated pixel positions to obtain the image pixels of the corrected x-ray image.

Moreover, in an example wherein the rotated pixel positions are located with uniform spacing, no further processing for determining corrected pixel positions is necessary. A rotated image is determined based on the plurality of rotated pixel positions. The rotated image is considered as the corrected x-ray image. In some embodiments, the rotated pixel positions may not be located with uniform spacing due to the rotation of the projection plane along one or more tilt axes. In such embodiments, the detector tilt correction unit 193 is further configured to modify the rotated pixel values of the rotated x-ray image to determine the corrected x-ray image. By way of a non-limiting example, the plurality of rotated pixel positions are interpolated to determine the plurality of corrected pixel positions. The term interpolation as used herein refers to determining intermediate pixel positions and corresponding pixel values in the rotated x-ray image. In one example, the plurality of rotated pixel values may be resampled using an interpolation technique to obtain the corrected pixel positions. Other examples of interpolation techniques that may be used for resampling the plurality of rotated pixels to determine the corrected pixel positions include, but are not limited to, a bicubic interpolation technique, a bilinear sampling technique, a nearest neighborhood sampling technique, and the like.

In one example, a plurality of interpolating techniques corresponding to a plurality of tilt axes may be used to resample the plurality of rotated pixels to determine the corresponding plurality of corrected pixel positions. In one example, a first pixel value corresponding to each pixel position among the plurality of corrected pixel positions may be generated using a first interpolation technique. The first interpolation technique is selected based on each pixel position and the first tilt axis. In addition, a second pixel value corresponding to each pixel position may be determined using a second interpolation technique. The second interpolation technique is selected based on each pixel position and the second tilt axis. The corrected x-ray image is generated based on a plurality of second pixel values corresponding to the plurality of corrected pixel positions.

The image processor 192 is communicatively coupled to the detector tilt correction unit 193 and configured to receive the corrected x-ray image 126 from the detector tilt correction unit 193. In some examples, the image processor 192 is configured to identify a medical condition of the anatomical region 110 of the subject 112 based on the corrected x-ray image. In one embodiment, the image processor 192 is configured to display the corrected x-ray image, the identified medical condition, or a combination thereof on the display device 195. To that end, the image processor 192 processes the corrected x-ray image with one or more image processing techniques, including but not limited to segmentation techniques, deep learning techniques, and so on.

In some examples, the display device 195 may be integrated with the user interface 183. For example, the display device 195 may comprise a touch-sensitive display device or a touchscreen, such that the display device 195 may display a graphical user interface and detect inputs by an operator. An example of a graphical user interface for embodiments wherein the display device 195 comprises a touch-sensitive display device is described further herein with regard to FIGS. 14 and 15.

Further, the processor 181 is communicatively coupled to the detector tilt correction unit 193, the memory unit 182, and the image processor 192 via a communication bus 182 and configured to provide computing and control functionalities. The processor 181 includes at least one of a central processing unit (CPU), a graphics processing unit (GPU), a digital signal processor, and a controller. In other embodiments, the processor 181 includes a customized processor element such as, but not limited to, an application-specific integrated circuit (ASIC) and a field-programmable gate array (FPGA). The processor 181 may be further configured to receive commands and/or parameters from an operator via the user interface 183. In some embodiments, the processor 181 may perform one or more functions of at least one of the image acquisition unit 102 and the detector tilt correction unit 193. The processor 181 may include more than one processor cooperatively working with each other for performing the functions described herein. The processor 181 may also be configured to store and retrieve contents into and from the memory 182. In one example, the processor 181 is configured to initiate and control the functionality of at least one of the image acquisition unit 102 and the detector tilt correction unit 193.

In one embodiment, the memory 182 comprises a random-access memory (RAM), read-only memory (ROM), flash memory, or any other type of computer-readable memory accessible by one or more of the image acquisition unit 102, the detector tilt correction unit 193, the image processor 192, and the processor 181. Also, in some examples, the memory 182 comprises a non-transitory computer-readable medium encoded with a program having a plurality of instructions to instruct at least one of the image acquisition unit 102, the detector tilt correction unit 193, the image processor 192, and the processor 181 to perform a sequence of steps to generate the corrected x-ray image. The program may further instruct the display device 195 to display the corrected x-ray image to the operator for evaluation of the corrected x-ray image.

As noted hereinabove, any misalignment between the detector plane 118 of the x-ray detector 108 and the x-ray source 104 results in tilt image artifacts in the resulting x-ray image. In accordance with aspects of the present disclosure, the detector tilt correction unit 193 is configured to detect and correct any tilt image artifacts in the x-ray image to generate a corrected x-ray image. To that end, the detector tilt correction unit 193 is configured to receive the x-ray image acquired via the x-ray detector 108 and the x-ray data acquisition unit 191. Additionally, the detector tilt correction unit 193 receives one or more tilt parameters from the user interface 183, in some examples, and additionally or alternatively automatically determines one or more tilt parameters by analyzing shadows of objects positioned between the subject 112 and the x-ray detector 108. For example, as described further herein with regard to FIGS. 2-9, a plurality of markers may be positioned on the surface of the x-ray detector 108 which block a small subset of x-rays in the x-ray beam 106 from reaching the x-ray detector 108, thereby casting a plurality of shadows in the resulting x-ray image. The detector tilt correction unit 193 may then analyze the positions and sizes of each shadow to determine an amount of detector tilt, as described further herein.

In some examples, a tilt of the x-ray detector 108 relative to the x-ray source 104 may be detected based on markers positioned on a surface of the x-ray detector 108. As an illustrative and non-limiting example, FIG. 2 shows a diagram 200 illustrating an example x-ray detector 208 configured with a plurality of markers for detecting tilt according to an embodiment. As depicted, the x-ray detector 208 is configured with a first marker 211, a second marker 212, a third marker 213, and a fourth marker 214 on a detector surface 220 of the x-ray detector 208. The markers 211, 212, 213, and 214 comprise physical, three-dimensional structures which extend or protrude away from the detector surface 220. The markers 211, 212, 213, and 214 may comprise lead, as an illustrative example, or another material capable of attenuating x-rays.

Further, as depicted, the markers 211, 212, 213, and 214 are positioned at respective corners of the detector surface 220, away from the center of the detector surface 220. In this way, if the center of the x-ray detector 208 is aligned with an x-ray source, such as x-ray source 104, and the region of interest of the object to be imaged is positioned in between the x-ray source and the x-ray detector 208, the markers 211, 212, 213, and 214 do not interfere, or at least minimally interfere, with x-rays generated by the x-ray source and attenuated by the object before impinging upon the detector surface 220 of the x-ray detector 208. That is, the markers 211, 212, 213, and 214 are positioned on the detector surface 220 such that sufficient area of the detector surface 220 is available for detecting x-rays attenuated by the region of interest of the subject being imaged. In other words, the field of view of the x-ray beam may be maintained in the center of the detector surface 220.

The diagram 200 in particular depicts the x-ray detector 208 without incident x-rays impinging thereon. FIG. 3 shows a diagram 300 illustrating the example x-ray detector 208 with shadows of the markers resulting from no detector tilt. In particular, as the markers 211, 212, 213, and 214 are configured to attenuate x-rays, the first marker 211 creates a first shadow 311, the second marker 212 creates a second shadow 312, the third marker 213 creates a third shadow 313, and the fourth marker 214 creates a fourth shadow 314 on the detector surface 220 of the x-ray detector 208.

Tilt of the detector 208 relative to the x-ray source may thus be detected based on the shapes and positions of shadows cast by the markers 211, 212, 213, and 214 on the detector surface 220. Specifically, assuming the x-ray source is aligned with the center of the x-ray detector, and that the x-ray detector is not tilted with respect to the x-ray source (e.g., the detector plane 118 or the detector surface 220 of the x-ray detector 208 is parallel to an x-ray emitting surface of the x-ray source), the shadows 311, 312, 313, and 314 cast by the markers 211, 212, 213, and 214 respectively extend an equal distance towards the corners of the detector surface 220 from the markers 211, 212, 213, and 214. As the shadows 311, 312, 313, and 314 appear in the resulting x-ray image, a method for detecting detector tilt may include segmenting the shadows in the x-ray image and analyzing the shapes and positions of the shadows to determine whether the detector 208 is tilted as well as the particular tilt angle and tilt direction of the detector 208 relative to the x-ray source.

In contrast with the shadows of the markers as depicted in the diagram 300, FIG. 4 shows a diagram 400 illustrating the example x-ray detector 208 with shadows of the markers resulting from vertical tilt. In particular, the first marker 211 creates a first shadow 411, the second marker 212 creates a second shadow 412, the third marker 213 creates a third shadow 413, and the fourth marker 214 creates a fourth shadow 414 on the detector surface 220 of the x-ray detector 208. As depicted, the first shadow 411 and the second shadow 412 are shorter and smaller than the first shadow 311 and the second shadow 312 created in the absence of detector tilt, while the third shadow 413 and the fourth shadow 414 are longer than the third shadow 313 and the fourth shadow 313 created in the absence of detector tilt.

By segmenting the shadows 411, 412, 413, and 414 from the resulting x-ray image and analyzing the sizes and positions, relative to each other as well as to the shadows 311, 312, 313, and 314 for no detector tilt, a method for detecting detector tilt may accurately determine the amount of detector tilt as well as the particular direction of the detector tilt with respect to the x-ray source.

The size and shape of markers positioned on the detector surface of an x-ray detector may be configured such that the shadows of the markers overlap the detector surface and therefore appear in the resulting x-ray images acquired via the x-ray detector. For example, the markers may be shaped as hemispheres, pyramids, triangles, and so on. However, spherical markers create circular shadows which may be difficult to discern from the real x-ray image data, and so pyramid shapes may be preferable for creating triangular shadows that are more easily distinguished and segmentable in the x-ray images. The markers 211, 212, 213, and 214 in the example embodiment depicted in FIGS. 2-4 comprise pyramid-shaped markers which create the triangular shadows shown in FIGS. 3 and 4. Further, in some examples the x-ray detector may be pressed against the subject being imaged, and for instances wherein the subject being imaged is a human or animal, the presence of the markers on the detector surface may cause discomfort to the subject. In such examples, a thin and smooth marker may be desirable.

As mentioned above, the tilt of an x-ray detector relative to an x-ray source may be determined based on the positions shadows created by markers positioned on the detector surface of the x-ray detector.

Figure 5:
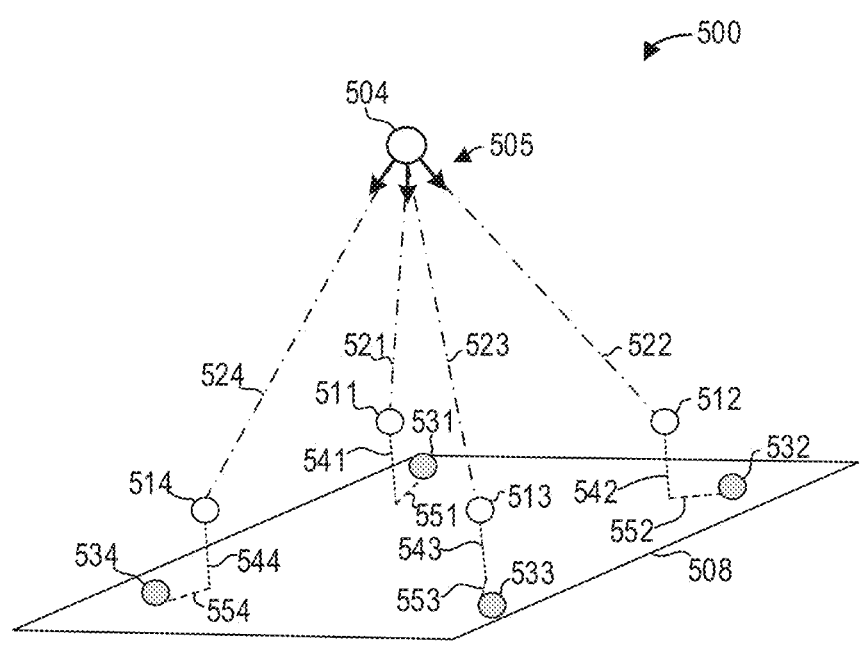
FIG. 5 shows a block diagram illustrating shadow positions on an x-ray detector with markers for detecting tilt according to an embodiment.

FIG. 5 shows a block diagram 500 illustrating shadow positions on an x-ray detector 508 with markers for detecting tilt according to an embodiment. In particular, the block diagram 500 depicts markers as point markers or elevated points positioned above the surface of the x-ray detector 508, including a first marker 511, a second marker 512, a third marker 513, and a fourth marker 514. It should be appreciated that the markers 511, 512, 513, and 514, as depicted, may correspond to a furthest point of a solid marker fixedly coupled to the surface of the x-ray detector 508, for example the tip of a pyramid-shaped marker as depicted in FIGS. 2-4, and that the markers 511, 512, 513, and 514 are depicted as elevated points for simplicity.

The x-ray source 504 emits a plurality of x-rays 505 towards the x-ray detector 508. A subset of the plurality of x-rays 505 are blocked from reaching the surface of the x-ray detector 508 by the markers 511, 512, 513, and 514, thereby creating shadows in the resulting x-ray image. The position of the shadows in the resulting x-ray image correspond to the projected points depicted as shaded circles on the surface of the x-ray detector 508, including a first shadow 531 for the first marker 511, a second shadow 532 for the second marker 512, a third shadow 533 for the third marker 513, and a fourth shadow 534 for the fourth marker 514. In particular, an x-ray of the plurality of x-rays 505 traveling along the first source distance 521, or the distance from the x-ray source 504 to the first marker 511, is blocked from reaching the x-ray detector 508 by the first marker 511, thereby resulting in the first shadow 531. Similarly, an x-ray of the plurality of x-rays traveling along the second source distance 522 from the x-ray source 504 to the second marker 512 is blocked from reaching the x-ray detector 508 by the second marker 512, thereby resulting in the second shadow 532. An x-ray of the plurality of x-rays traveling along the third source distance 523 from the x-ray source 504 to the third marker 513 is blocked from reaching the x-ray detector 508 by the third marker 513, thereby resulting in the third shadow 533. An x-ray of the plurality of x-rays traveling along the fourth source distance 524 from the x-ray source 504 to the fourth marker 514 is blocked from reaching the x-ray detector 508 by the fourth marker 514, thereby resulting in the fourth shadow 534.

The positions of the markers 511, 512, 513, and 514 relative to the x-ray detector 508 are known, including the distance or height of the markers 511, 512, 513, and 514 from the surface of the x-ray detector 508. For example, the first marker 511 is a first elevation 541 away from the x-ray detector 508, the second marker 512 is a second elevation 542 away from the x-ray detector 508, the third marker 513 is a third elevation 543 away from the x-ray detector 508, and the fourth marker 514 is a fourth elevation 544 away from the x-ray detector 508. The elevations 541, 542, 543, and 544 of the markers 511, 512, 513, and 514 are the same distance, in some examples, though it should be appreciated that in other examples different configurations of relative marker positions may be used.

The tilt of the x-ray detector 508 relative to the x-ray source may thus be determined by measuring the distance of the shadows 531, 532, 533, and 534 from the corresponding markers 511, 512, 513, and 514. More specifically, since the elevations 511, 512, 513, and 514 are known, the surface distances 551, 552, 553, and 554 of the shadows 531, 532, 533, and 534, respectively, from the marker positions may be measured to determine the tilt of the x-ray detector 508. For example, if the x-ray source 504 is aligned with the center of the x-ray detector 508, and the x-ray detector 508 is not tilted with respect to the x-ray source 504, then the surface distances 551, 552, 553, and 554 are equal. In contrast, if the x-ray detector 508 is tilted such that the first marker 511 is closer to the x-ray source 504 while the third marker 513 is further from the x-ray source 504, as an illustrative example, then the first surface distance 551 of the first shadow 531 is shortened while the third surface distance 553 of the third shadow 533 is lengthened with respect to the surface distances for no tilt. Thus, by measuring the first surface distance 551 of the first shadow 531, the second surface distance 552 of the second shadow 532, the third surface distance 553 of the third shadow 533, and the fourth surface distance 554 of the fourth shadow 534, as well as the distance of the x-ray source 504 from the center of the x-ray detector 508, the angles and direction of detector tilt can be determined.

Figure 6:
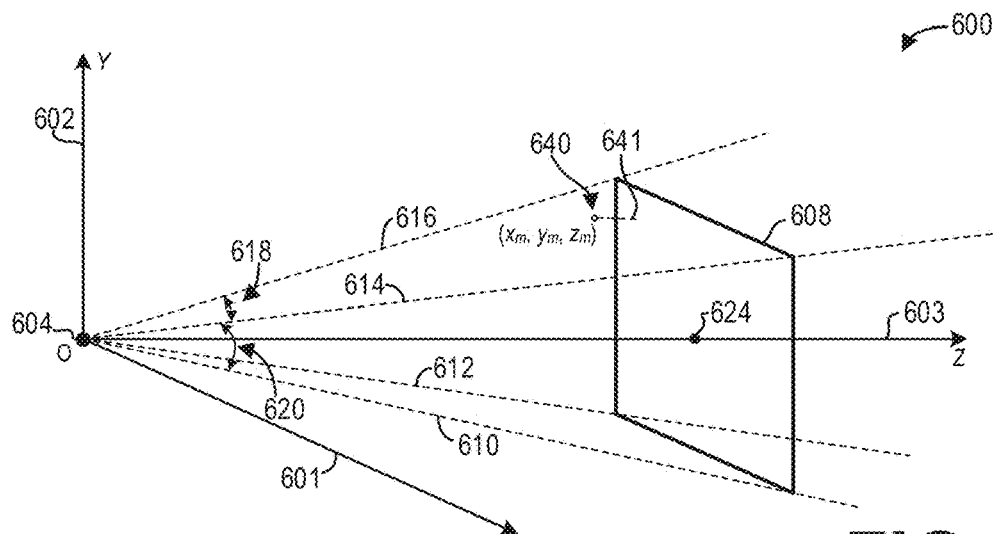
FIG. 6 shows a diagram illustrating geometrical analysis of marker shadows in three-dimensional space according to an embodiment.
Figure 7:
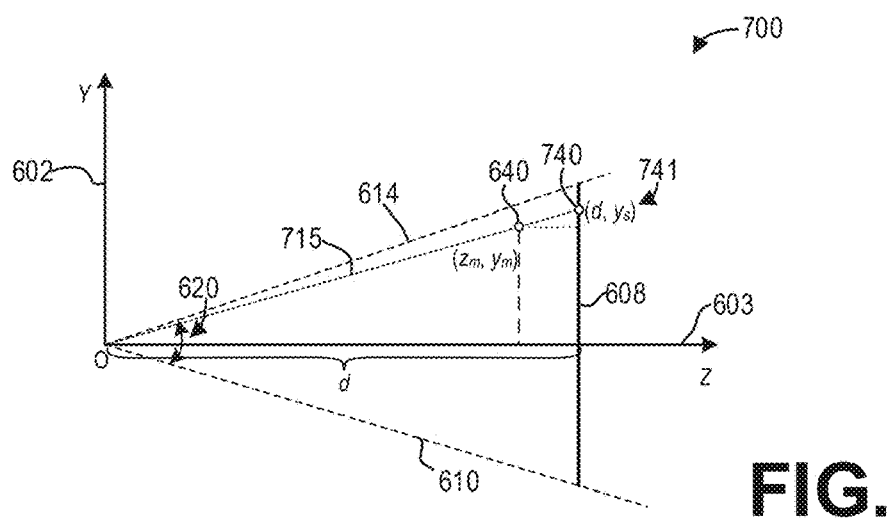
FIG. 7 shows a diagram illustrating the geometrical analysis of marker shadows in a first plane according to an embodiment.
Figure 8:
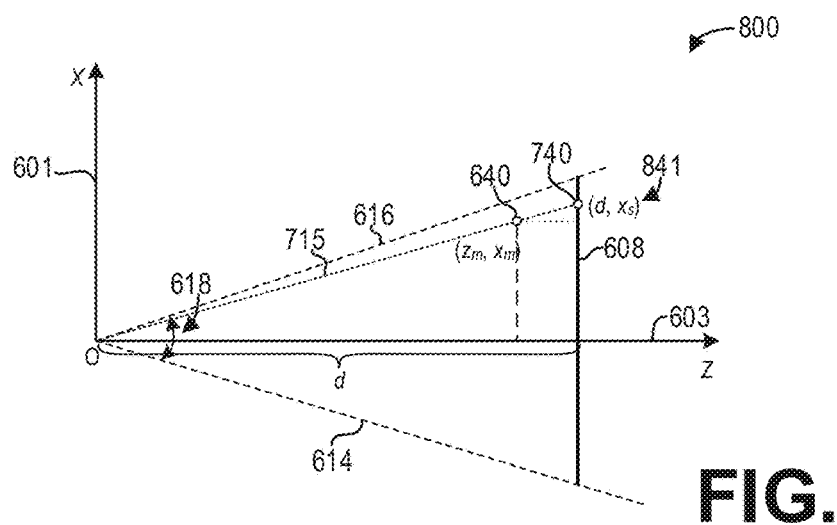
FIG. 8 shows a diagram illustrating the geometrical analysis of marker shadows in a second plane according to an embodiment.

To further illustrate the marker-based approach for determining detector tilt, FIGS. 6-8 illustrative a geometrical analysis of marker shadows in three-dimensional space. In particular, FIG. 6 shows a diagram 600 illustrating geometrical analysis of marker shadows in three-dimensional space according to an embodiment. The diagram 600 depicts a three-dimensional coordinate system including a first axis 601 or the x-axis, a second axis 602 or the y-axis, and a third axis 603 or the z-axis, with an x-ray source 604 positioned at the origin O of the coordinate system. An x-ray detector 608 is positioned a distance d away from the x-ray source 604, with the center 624 of the x-ray detector 608 positioned on the third axis 603 such that the x-ray source 604 is aligned with the center 624 of the x-ray detector 608.

The diagram 600 further depicts paths of a first x-ray 610, a second x-ray 612, a third x-ray 614, and a fourth x-ray 616 that originate from the x-ray source 604 and intersect respective corners of the x-ray detector 608. The field of view 618 of the x-ray source 604 in the x direction or along the first axis 601 therefore extends from the third x-ray 614 to the fourth x-ray 616, and similarly from the first x-ray 610 to the second x-ray 612. The field of view 620 in the y direction or along the second axis 602 extends from the first x-ray 610 to the third x-ray 614, and similarly from the second x-ray 612 to the fourth x-ray 616.

The diagram 600 further depicts a point marker 640, also referred to herein simply as a marker 640, positioned a height 641 away from the surface of the x-ray detector 608 with position coordinates ($x_m$, $y_m$, $z_m$), wherein $x_m$ is the distance of the marker 640 from the origin O on the first axis 601, $y_m$ is the distance of the marker 640 from the origin O on the second axis 602, and $z_m$ is the distance of the marker 640 from the origin O on the third axis 603.

FIG. 7 shows a diagram 700 illustrating the geometrical analysis of marker shadows in a first plane, namely the y-z plane defined by the second axis 602 and the third axis 603. The diagram 700 depicts a projected position 741 of a shadow 740 of the marker 640 on the x-ray detector 608 in the first plane. The projected position 741 of the shadow 740 of the marker 640 on the x-ray detector 608 corresponds to a projection onto the x-ray detector 608 of an x-ray 715 originating from the x-ray source 604 at the origin O and intersecting the marker 640, as depicted.

Further, FIG. 8 shows a diagram 800 illustrating the geometrical analysis of marker shadows in a second plane, namely the x-z plane defined by the first axis 601 and the third axis 603. The diagram 800 depicts a projected position 841 of the shadow 740 of the shadow of the marker 640 on the x-ray detector 608 in the second plane. Similar to FIG. 7, the projected shadow position 841 of the shadow 740 of the marker 640 on the x-ray detector 608 corresponds to a projection onto the x-ray detector 608 of the x-ray 715 originating at the x-ray source 604 at the origin O and intersecting the marker 640, as depicted.

As depicted in FIG. 7, the position of the marker 640 in the first plane is given by ($z_m$, $y_m$) while the projected position 741 of the shadow 740 in the first plane is given by (d, $y_s$), wherein $y_s$ is the distance of the shadow 740 from the origin O along the second axis 602 and d is the distance of the x-ray detector 608 from the origin O along the third axis 603. According to the ratio of similar triangles, $$\frac{y_s}{y_m} = \frac{d}{z_m}.$$

Therefore, the distance $y_s$ of the shadow 740 from the origin O along the second axis 602 when there is no detector tilt is:

$$y_s = d\frac{y_m}{z_m}.$$

Similarly, as depicted in FIG. 8, the position of the marker 640 in the second plane is given by ($z_m$, $x_m$) while the projected position 841 of the shadow 740 in the second plane is given by (d, $x_s$), where $x_s$ is the distance of the shadow 740 from the origin O along the first axis 601. According to the ratio of similar triangles, as used above for the distance $y_s$, the distance $x_s$ of the shadow 740 from the origin O along the first axis 601 when there is no detector tilt is:

$$x_s = d\frac{x_m}{z_m}.$$

If the position of the marker 640 relative to the x-ray detector 608 is known and the distance d of the x-ray detector 608 from the x-ray source 604 is measured, then the projected position of the shadow 740 given by ($x_s$, $y_s$, $z_s$=d) is known. If the x-ray detector 608 is tilted with respect to the x-ray source 104, the expressions for determining the position of the shadow 740 provided hereinabove are not valid since $z_s$ is not equal to d when the x-ray detector 608 is tilted. Nevertheless, the angle and direction of detector tilt can be determined by comparing the position of the marker shadows in the presence of detector tilt to the projected position of marker shadows in the absence of detector tilt.

Further, the expressions provided hereinabove for determining the position of the shadow 740 may be used to configure the size of the markers. For example, if the marker 640 comprises a line marker extending from the surface of the x-ray detector 608 with a height 641 of two centimeters, and the distance d of the x-ray detector 608 from the x-ray source 604 is 120 centimeters, then the marker 640 is 118 centimeters from the x-ray source 604. Further, if the marker 640 is positioned 12 centimeters from the center 624 of the x-ray detector 608 along the second axis 602, then the length L of the shadow of the marker 640 in the y direction is:

$$L = y_s - y_m = d\frac{y_m}{z_m} - y_m = (120 \text{ cm})\frac{12 \text{ cm}}{118 \text{ cm}} - 12 \text{ cm} = 0.20 \text{ cm}.$$

Assuming that the pixel resolution of the x-ray detector 608 is, as an illustrative example, 250 pixels per inch or approximately 98 pixels per centimeter, then the shadow length L of 0.20 centimeters is approximately 20 pixels in length. As such, the segmentation algorithm for segmenting the shadow from an x-ray image to determine detector tilt should be capable of segmenting shadows 20 pixels in size. The sensitivity of the segmentation algorithm to segmenting shadows less than 20 pixels in size or more than 20 pixels in size may therefore be considered when configuring the size and shape of the markers for positioning on the surface of an x-ray detector.

Figure 9:
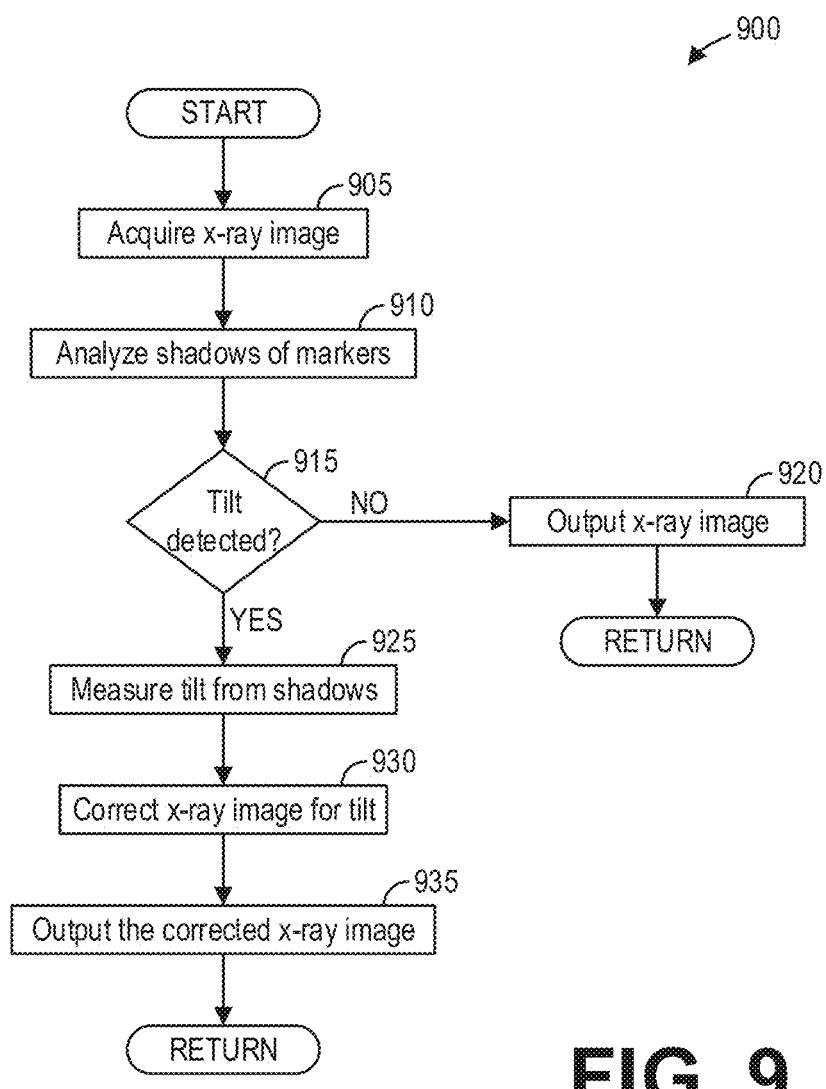
FIG. 9 shows a high-level flow chart illustrating an example method for detecting and correcting detector tilt based on marker shadows according to an embodiment.

FIG. 9 shows a high-level flow chart illustrating an example method 900 for detecting and correcting detector tilt based on marker shadows according to an embodiment. In particular, method 900 relates to analyzing shadows of markers to determine an amount of detector tilt and correcting an x-ray image according to the amount of detector tilt. Method 900 is described with regard to the systems and components of FIGS. 1-8, though it should be appreciated that the method may be implemented with other systems and components without departing from the scope of the present disclosure. Method 900 may be implemented as executable instructions in non-transitory memory, such as memory 182, and may be executed by a processor, including one or more of the processor 181, the image processor 192, or the detector tilt correction unit 193, of an x-ray imaging system, such as the x-ray imaging system 100.

Method 900 begins at 905. At 905, method 900 acquires an x-ray image of an object 110. To that end, the object 110, which may comprise a region of interest 110 of the subject 112, is positioned between the x-ray source 104 and the x-ray detector 108. With the subject 112 positioned between the x-ray source 104 and the x-ray detector 108, method 900 controls the x-ray controller 187 to drive the x-ray source 104 to generate an x-ray beam 106 towards the object 110. X-rays of the x-ray beam 106 attenuated by the object 110 are then detected by the x-ray detector 108, and the x-ray image corresponding to the detected x-rays are recorded by the x-ray data acquisition unit 191. The x-ray detector 108 is configured with a plurality of markers, such as the markers 211, 212, 213, and 214 of FIGS. 2-4 as an example, fixedly attached to the surface of the x-ray detector 108. As each marker of the plurality of markers is configured to block x-ray transmission, the x-ray image acquired via the x-ray detector includes a plurality of shadows corresponding to the plurality of markers.

In some examples, method 900 further receives one or more imaging parameters from one or more of the image acquisition unit 102 and the user interface 183. As illustrative and non-limiting examples, the one or more imaging parameters may include a first field-of-view angle, a second field-of-view angle, source coordinates representative of a position of the x-ray source 104, and detector coordinates representative of a position of the x-ray detector 108. In some examples, the one or more imaging parameters includes a distance between the x-ray source 104 and the x-ray detector 108. In other examples, the distance between the x-ray source 104 and the x-ray detector 108 may be derived from the source coordinates and the detector coordinates.

Continuing at 910, method 900 analyzes shadows of markers. In some examples, method 900 may segment the shadows of the markers in the x-ray image to obtain shadow segments. Method 900 then measures the size of each shadow in either the shadow segments or directly in the x-ray image. Method 900 may further determine the direction of the shadows from the marker position relative to the x-ray detector 108.

At 915, method 900 determines if tilt is detected. Method 900 determines if tilt is detected based on the shadows of the markers. Method 900 detects tilt if a size and/or direction of one or more of the shadows deviates from an expected size and/or direction of the shadows. Thus, method 900 may initially determine the expected size and/or direction of the shadows based on the distance of the x-ray detector 108 from the x-ray source 104, as well as the known geometry of the markers. For example, method 900 may calculate an expected position of a shadow for a particular point of the marker (e.g., the tip of the marker) in the horizontal or x direction according to:

$$x_s = d\frac{x_m}{z_m},$$

as discussed hereinabove, wherein d is the distance of the x-ray detector 108 from the x-ray source 104 along the z axis, $z_m$ is the distance of the particular point of the marker from the x-ray source 104 along the z axis, and $x_m$ is the distance of the marker from the center of the x-ray detector 108. As $x_m$ is known and $z_m$ is determined from the distance d, the expected position of the shadow of the particular point of the marker is easily calculated according to the expression above. The expected position of the shadow for the particular point of the marker in the vertical or y direction is similarly calculated, as discussed hereinabove. Thus, method 900 may calculate the expected positions of shadows of the markers, and compare the actual shadows analyzed at 910 to the expected positions. In other examples, the expected positions of shadows may be predetermined for a plurality of distances d and stored in a lookup table. In such examples, method 900 may retrieve expected positions of the shadows for the given distance d from the lookup table. Further, the method for determining the excepted positions of shadows for particular points of a marker may be applied to each point of a marker, thereby providing an expected size and direction of the shadow of the marker in an x-ray image, assuming that the x-ray source 104 and the x-ray detector 108 are aligned on the z-axis and that the detector plane 118 of the x-ray detector 108 is not tilted.

As mentioned above, determining if a tilt is detected comprises determining if the size and/or direction of the shadows of the markers deviate from an expected size and/or direction of the shadows. If the size and the direction of the shadows do not deviate from the expected size and direction of the shadows, then detector tilt is not detected ("NO"), and method 900 proceeds to 920. At 920, method 900 outputs the x-ray image, for example to the display device 195 for display. Method 900 then returns.

However, referring again to 915, if the size and/or direction of the shadows deviate from the expected size and/or direction of the shadows, then tilt is detected ("YES"), and method 900 proceeds to 925. At 925, method 900 measures the tilt from the shadows. In particular, method 900 calculates at least one tilt angle in at least one direction based on the size and/or direction of the shadows of the markers. For example, method 900 may calculate one or more of a first tilt angle, a second tilt angle, and a third tilt angle of the x-ray detector 108 in one or more of the first tilt axis, the second tilt axis, or the third tilt axis, respectively, as described hereinabove.

At 930, method 900 corrects the x-ray image for the tilt. In some examples, method 900 transforms the image data of the x-ray image from the detector plane 118 to a corrected detector plane 145 by rotating the image data along one or more axes, for example by use of one or more rotation matrices, according to the one or more tilt angles calculated based on the size and/or direction of the shadows. For example, as described hereinabove, method 900 may determine a perspective projection of the detector plane 118 in the field of view of the x-ray beam 106 to determine a projection plane, wherein the detector plane 118 includes a plurality of image pixels that correspond to a plurality of image pixel positions in the detector plane 118. Further, method 900 rotates the projection plane to the corrected detector plane 145 using one or more rotation matrices, wherein the corrected detector plane 145 includes a plurality of rotated pixel positions. Method 900 then assigns the plurality of image pixel values to a plurality of rotated pixel values in the corrected detector plane 145, wherein the plurality of rotated pixels correspond to the plurality of rotated pixel positions. Method 900 may then interpolate the plurality of rotated pixels to generate the plurality of corrected pixels, and may further interpolate the plurality of rotated pixel positions to generate the plurality of corrected pixel positions.

At 935, method 900 outputs the corrected x-ray image, for example to the display device 195 for display to the user. Method 900 then returns.

Thus, systems and methods are provided for detecting and correcting detector tilt in x-ray imaging systems. In one embodiment, a method comprises acquiring, with an x-ray detector tilted at an angle with respect to an x-ray source, an x-ray image, calculating the angle from the x-ray image, generating a corrected x-ray image based on the calculated angle, and displaying the corrected x-ray image, wherein the x-ray detector is configured with a plurality of markers positioned at a detecting surface of the x-ray detector, and calculating the angle from the x-ray image comprises measuring positions of a plurality of shadows in the x-ray image caused by the plurality of markers.

In other examples, an anti-scatter grid may be used instead of markers for detecting and correcting detector tilt.

Anti-scatter grids are typically used for improving image quality for x-ray imaging by permitting transmission of primary radiation and selectively rejecting scattered radiation. As an illustrative example, FIG. 10 shows a diagram 1000 illustrating an example position of an anti-scatter grid 1015 relative to an x-ray source 1004, an x-ray detector 1008, and a subject 1010 being imaged according to an embodiment. The anti-scatter grid 1015 comprises a plurality of shielding strips 1017, for example, to permit transmission of primary radiation such as the plurality of x-rays 1006 emitted by the x-ray source 1004 to the x-ray detector 1008, while selectively blocking or shielding scattered radiation such as scattered x-rays 1026 from reaching the x-ray detector 1008.

The plurality of shielding strips 1017 may be arranged with a linear geometry in one direction, and furthermore may be arranged according to the trajectories of the x-rays 1006 generated by the x-ray source 1004. For example, if the trajectories of the plurality of x-rays 1006 are parallel, the plurality of shielding strips 1017 may be arranged accordingly to form the anti-scatter grid 1015, in some examples. As another example, the plurality of shielding strips 1017 may be arranged to be parallel near the center along the x-ray central axis and progressively slanted toward the periphery of the anti-scatter grid 1015, for example as depicted, to match the beam divergence of the plurality of x-rays 1006. Furthermore, the plurality of shielding strips 1017 may be arranged in a cross-hatched grid, such that shielding strips 1017 are arranged in two perpendicular directions. The particular geometrical arrangement of the plurality of shielding strips 1017 thus may be configured or adapted according to the type of x-ray source 1004. Furthermore, the plurality of shielding strips may comprise a material suitable for blocking x-ray radiation, such as lead as an illustrative example.

While improving image quality by preventing the scattered x-rays 1026 from reaching the x-ray detector 1008, the anti-scatter grid 1015 also prevents transmission of primary x-rays that are incident directly on the lead strips, thereby resulting in a shadow of the anti-scatter grid 1015 in an x-ray image acquired by the x-ray detector 1008.

As an illustrative example, FIG. 11 shows a diagram illustrating an example grid pattern 1100 formed by an anti-scatter grid such as the anti-scatter grid 1015 in the absence of detector tilt according to an embodiment. In some examples, the plurality of shielding strips 1017 of the anti-scatter grid 1015 are configured such that, in the absence of detector tilt, the grid pattern 1100 appears in an x-ray image acquired by an x-ray detector, such as the x-ray detector 1008, shielded from scatter radiation by the anti-scatter grid 1015. The grid pattern 1100 includes a plurality of vertical lines 1102 as well as a plurality of horizontal lines 1112, wherein each of the plurality of vertical lines 1102 are parallel to each other vertical line and perpendicular to each horizontal line of the plurality of horizontal lines 1112, wherein each horizontal line is also parallel to each other horizontal line.

Typically, after acquiring an x-ray image with an x-ray detector 1008 shielded by an anti-scatter grid 1015, the grid pattern 1100 is removed from the x-ray image by conditioning or processing the x-ray image. However, in some examples, a method for detecting and correcting detector tilt includes analyzing the grid pattern formed by an anti-scatter grid to determine whether the x-ray detector is tilted during the acquisition of the x-ray image. For example, in the presence of vertical detector tilt or a pitch of the detector plane, at least a subset of the horizontal lines 1112 may appear closer to each other towards one end of the x-ray image while another subset of the horizontal lines 1112 may appear further apart towards an opposite end of the x-ray image, and the spacing of the vertical lines 1102 may remain as depicted in the grid pattern 1100.

Similarly, in the presence of horizontal or lateral detector tilt or a roll of the detector plane, at least a subset of the vertical lines 1102 may be closer together towards one end of the x-ray image. As an illustrative and non-limiting example, FIG. 12 shows a diagram illustrating an example grid pattern 1200 formed by an anti-scatter grid, such as the anti-scatter grid 1015, in the presence of lateral detector tilt according to an embodiment. As depicted, a subset 1204 of the plurality of vertical lines 1102 are increasingly positioned closer together towards one end of the grid pattern 1200 which may appear in an x-ray image acquired with an x-ray detector tilted laterally with respect to an x-ray source.

Further, in the presence of detector tilt in multiple directions (e.g., pitch and roll or in the vertical and horizontal directions), the resulting grid pattern will correspond to the amount of detector tilt in each direction. As discussed further herein, the amount of tilt in both directions may be independently obtained from analysis of the grid pattern caused from an anti-scatter grid in an x-ray image.

Figure 13:
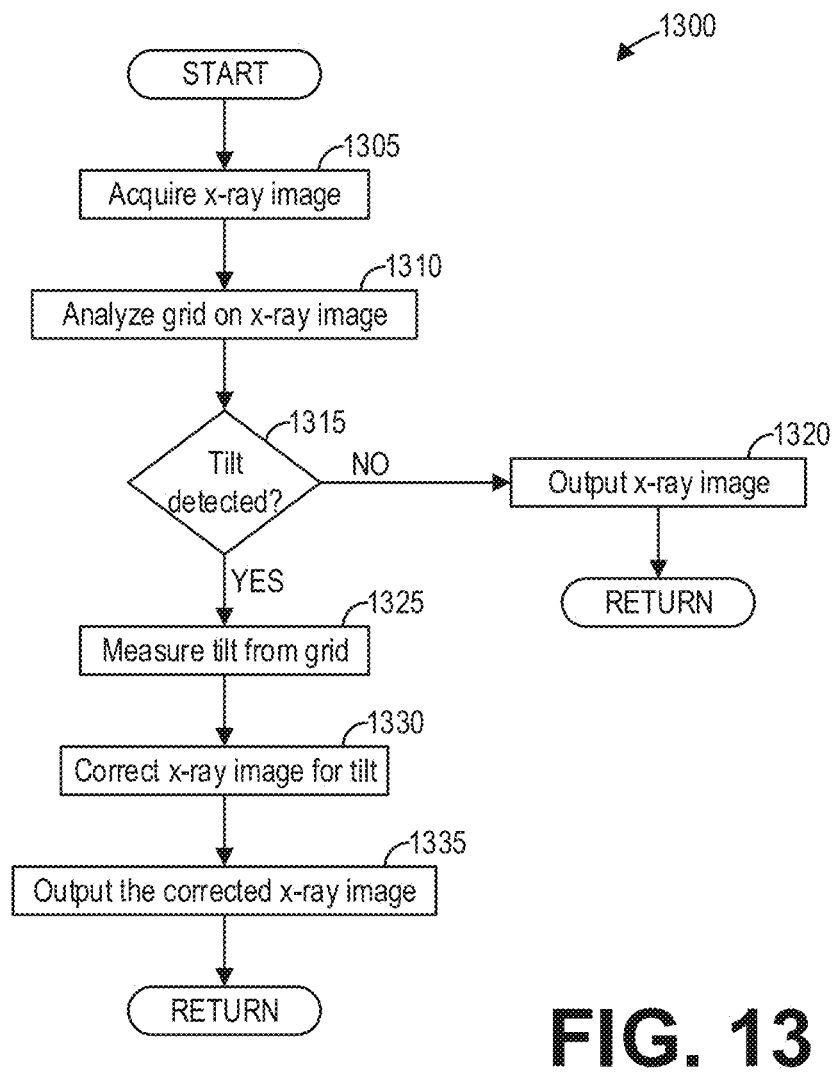
FIG. 13 shows a high-level flow chart illustrating an example method for detecting and correcting detector tilt based on an anti-scatter grid according to an embodiment.

FIG. 13 shows a high-level flow chart illustrating an example method 1300 for detecting and correcting detector tilt based on an anti-scatter grid according to an embodiment. In particular, method 1300 relates to analyzing shadows of an anti-scatter grid to determine an amount of detector tilt and correcting an x-ray image according to the amount of detector tilt. Method 1300 is described with regard to the systems and components of FIGS. 1 and 10-12, though it should be appreciated that the method 1300 may be implemented with other systems and components without departing from the scope of the present disclosure. Method 1300 may be implemented as executable instructions in non-transitory memory, such as memory 182, and may be executed by a processor, including one or more of the processor 181, the image processor 192, or the detector tilt correction unit 193, of an x-ray imaging system, such as the x-ray imaging system 100.

Method 1300 begins at 1305. At 1305, method 1300 acquires an x-ray image of an imaging subject or an object 110. To that end, the object 110, which may comprise a region of interest 110 of the subject 112, is positioned between the x-ray source 104 and the x-ray detector 108. With the subject 112 positioned between the x-ray source 104 and the x-ray detector 108, method 1300 controls the x-ray controller 187 to drive the x-ray source 104 to generate an x-ray beam 106 towards the object 110. X-rays of the x-ray beam 106 attenuated by the object 110 are then detected by the x-ray detector 108, and the x-ray image corresponding to the detected x-rays are recorded by the x-ray data acquisition unit 191. An anti-scatter grid, such as the anti-scatter grid 1015, is positioned between the object 110 and the x-ray detector 108, such that primary radiation of the x-ray beam 106 attenuated by the object 110 reaches the x-ray detector 108 while scattered radiation is shielded by the anti-scatter grid 1015. As the anti-scatter grid 1015 also blocks some primary radiation of the x-ray beam 106 from reaching the x-ray detector 108, the x-ray image acquired via the x-ray detector 108 includes a shadow or a plurality of shadows corresponding to the geometry of the anti-scatter grid 1015. That is, the x-ray image includes a grid pattern corresponding to the geometry of the anti-scatter grid 1015.

In some examples, method 1300 further receives one or more imaging parameters from one or more of the image acquisition unit 102 and the user interface 183. As illustrative and non-limiting examples, the one or more imaging parameters may include a first field-of-view angle, a second field-of-view angle, source coordinates representative of a position of the x-ray source 104, and detector coordinates representative of a position of the x-ray detector 108. In some examples, the one or more imaging parameters includes a distance between the x-ray source 104 and the x-ray detector 108. In other examples, the distance between the x-ray source 104 and the x-ray detector 108 may be derived from the source coordinates and the detector coordinates.

At 1310, method 1300 analyzes the grid on the x-ray image. As one example, method 1300 performs a fast Fourier transform (FFT) of the x-ray image to obtain a grid frequency characterizing the grid. An expected grid frequency for the anti-scatter grid in the absence of detector tilt is known and stored locally for reference. For different combinations of tilt in the horizontal and vertical directions, the grid frequency detected will have a larger spectrum than the expected grid frequency. The tilt angle can be calibrated with the frequency drift in both axes independently, so that horizontal shift and vertical shift vectors can be computed.

At 1315, method 1300 determines if tilt is detected. Method 1300 may determine that tilt is detected, for example, if the grid frequency measured in the x-ray image is different from the expected grid frequency of the anti-scatter grid. If tilt is not detected ("NO"), method 1300 continues to 1320. At 1320, method 1300 outputs the x-ray image, for example to the display device 195 for display to the user. Method 1300 may further process the x-ray image, for example by removing the grid from the image, prior to outputting the x-ray image to the display device. Method 1300 then returns.

However, referring again to 1315, if tilt is detected ("YES"), method 1300 continues to 1325. At 1325, method 1300 measures the tilt from the grid. For example, method 1300 may measure one or more tilt angles in one or more tilt axes based on the frequency drift of the grid frequency in the one or more tilt axes.

At 1330, method 1300 corrects the x-ray image for the tilt. In some examples, method 1300 transforms the image data of the x-ray image from the detector plane 118 to a corrected detector plane 145 by rotating the image data along one or more axes, for example by use of one or more rotation matrices, according to the one or more tilt angles calculated based on the shadows of the anti-scatter grid. For example, as described hereinabove, method 1300 may determine a perspective projection of the detector plane 118 in the field of view of the x-ray beam 106 to determine a projection plane, wherein the detector plane 118 includes a plurality of image pixels that correspond to a plurality of image pixel positions in the detector plane 118. Further, method 1300 rotates the projection plane to the corrected detector plane 145 using one or more rotation matrices, wherein the corrected detector plane 145 includes a plurality of rotated pixel positions. Method 1300 then assigns the plurality of image pixel values to a plurality of rotated pixel values in the corrected detector plane 145, wherein the plurality of rotated pixels correspond to the plurality of rotated pixel positions. Method 1300 may then interpolate the plurality of rotated pixels to generate the plurality of corrected pixels, and may further interpolate the plurality of rotated pixel positions to generate the plurality of corrected pixel positions. Further, after generating the corrected x-ray image, method 1300 further removes the grid pattern of the anti-scatter grid from the corrected x-ray image. In some examples, method 1300 may remove the grid pattern from the x-ray image prior to performing the tilt correction.

At 1335, method 1300 outputs the corrected x-ray image, for example to the display device 195 for display to the user. Method 1300 then returns.

Thus, methods and systems are provided for correcting detector tilt with an anti-scatter grid. In one embodiment, a method comprises acquiring, with an x-ray detector tilted at an angle with respect to an x-ray source, an x-ray image, calculating the angle from the x-ray image, generating a corrected x-ray image based on the calculated angle, and displaying the corrected x-ray image, wherein an anti-scatter grid is positioned adjacent to the x-ray detector during the acquisition of the x-ray image, and calculating the angle from the x-ray image comprises measuring shifts in a shadow of the anti-scatter grid in the x-ray image.

Figure 14:
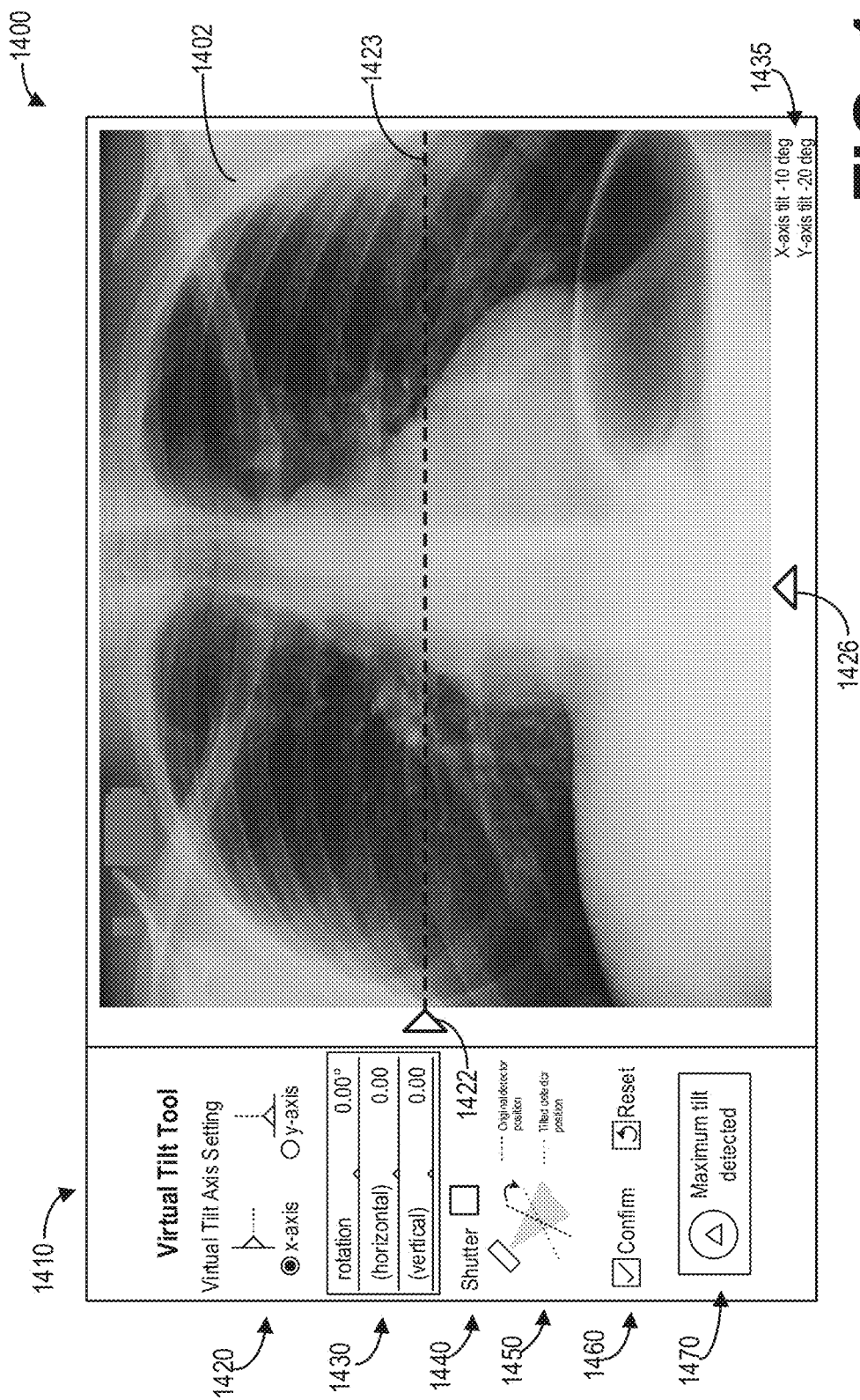
FIG. 14 shows a diagram illustrating an example graphical user interface for virtual tilt correction according to an embodiment.

While the systems and methods provided hereinabove enable the automatic detection and correction of x-ray detector tilt in acquired x-ray images, in some examples detector tilt may be manually corrected by a user of an x-ray imaging system. As an illustrative example, FIG. 14 shows a diagram illustrating an example graphical user interface 1400 for virtual tilt correction of an x-ray image 1402 according to an embodiment. The graphical user interface 1400 may be displayed, for example, via a display device 195 of an x-ray imaging system 100, and enables the user of the x-ray imaging system 100 to easily and intuitively tilt the x-ray image 1402 to a correct position.

The graphical user interface 1400 displays the x-ray image 1402 acquired with an x-ray detector such as x-ray detector 108. The graphical user interface 1400 further displays settings for a virtual tilt tool 1410 for correcting the detector tilt. The virtual tilt tool 1410 includes, as illustrative and non-limiting examples: an input 1420 for user selection of a virtual tilt axis; inputs 1430 for adjusting the rotation angle, the position of the horizontal tilt axis, and the position of the vertical tilt axis; an input 1440 for controlling a shutter of the x-ray source 104 for acquiring a new x-ray image; a visual output 1450 depicting the tilted detector position relative to the original detector position and the x-ray source; and an input 1460 for confirming or finalizing the virtual tilt control and resetting the settings.

The input 1460 for confirming or finalizing the virtual tilt control and resetting the settings allows the user to easily set the tilt per image, or to reset the tilt angles back to zero degrees. In some examples, tilt angles automatically determined from shadows such as marker shadows or grid shadows, as described hereinabove, may be automatically loaded in the virtual tilt tool 1410. The user may thus confirm the automatically-determined tilt angles, provide additional manual adjustments to the automatically-determined tilt angles, or reject the automatically-determined tilt angles.

In some examples, the graphical user interface 1400 further displays an alert 1470 indicating that a maximum tilt is detected when a virtual tilt input by the user is at a maximum tilt or within a threshold range of the maximum tilt. The graphical user interface 1400 further includes an output 1435 indicating virtual tilt angles in both the horizontal or x-axis as well as the vertical or y-axis. The graphical user interface 1400 further includes an input slider 1422 for controlling a position of the horizontal virtual tilt axis 1423, as well as an input slider 1426 for controlling a position of a vertical virtual tilt axis. As depicted, the horizontal virtual tilt axis is selected via the input 1420 for adjusting, and so the virtual tilt axis 1423 is also superimposed on the x-ray image 1402 to provide a visual reference.

The user of the x-ray imaging system 100 may thus select, via the input 1420, whether to rotate or tilt the x-ray image 1402 horizontally and/or vertically about the horizontal x-axis or the vertical y-axis. The user may further adjust the position of the x-axis or the y-axis for virtually tilting the x-ray image 1402, by adjusting the position of the input slider 1422 for the horizontal virtual tilt axis 1423 or the position of the input slider 1426 for the vertical virtual tilt axis. To tilt the x-ray image 1402 about the selected position of the selected virtual tilt axis, the user may adjust the slider position of the inputs 1430, as one example.

As another example, the graphical user interface 1400 is displayed via the display device 195 which in some examples comprises a touch-sensitive display device or a touchscreen display. The user may press the x-ray image 1402 in the graphical user interface 1400 to tilt the x-ray image 1402 about the selected position of the selected virtual tilt axis. More specifically, the user may press a point on the touchscreen or display device 195 corresponding to a region of the x-ray image 1402 displayed on the display device 195, and one or more of the processor 181, the image processor 192, and the detector tilt correction unit 193 tilt the x-ray image 1402 according to the region of the x-ray image 1402 pressed by the user.

Figure 15:
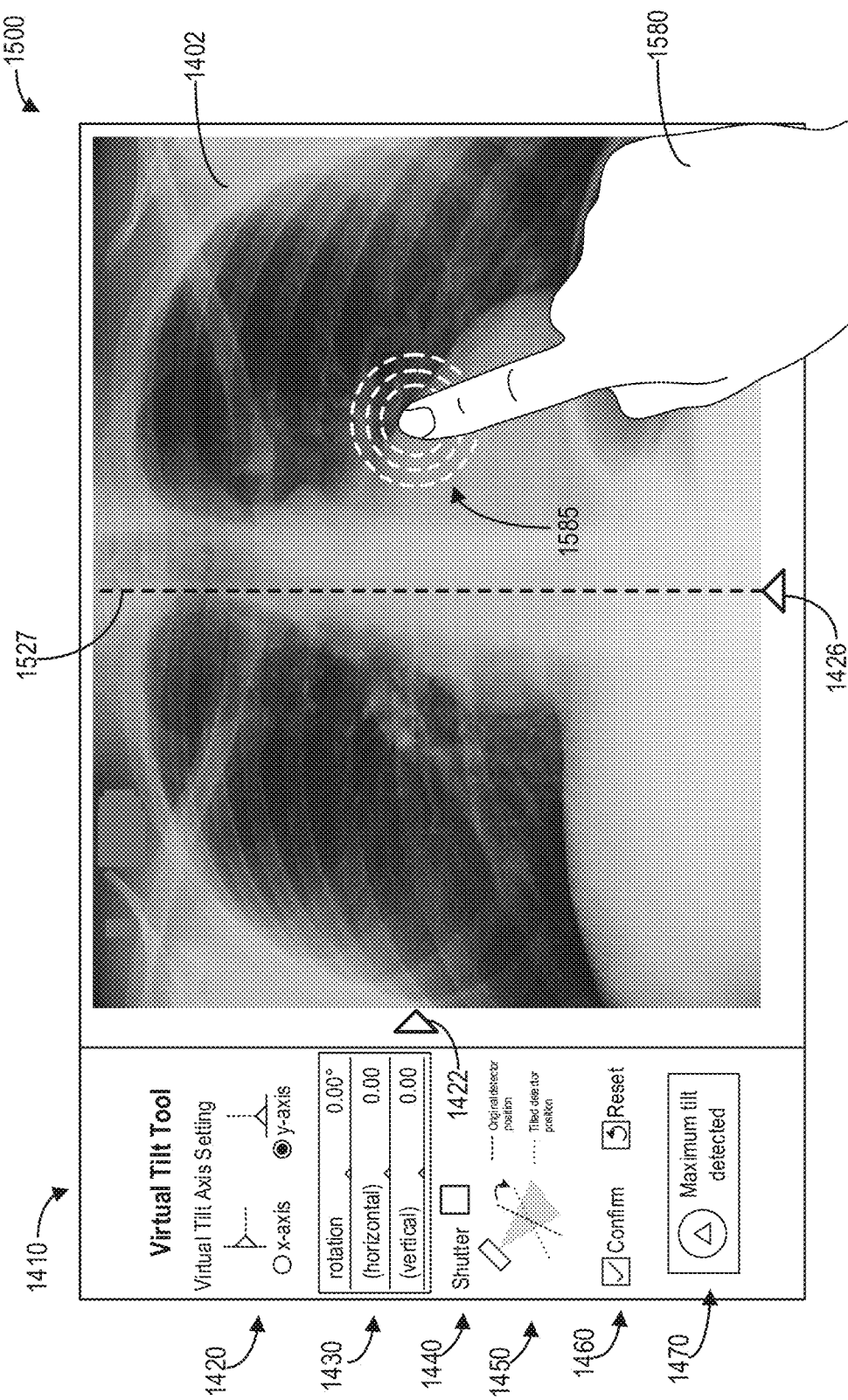
FIG. 15 shows a diagram illustrating the example graphical user interface of FIG. 14 with example user input according to an embodiment.

As an illustrative example, FIG. 15 shows a diagram illustrating an example graphical user interface 1500 corresponding to the graphical user interface 1400 with example user input according to an embodiment. As depicted, the vertical axis or the y-axis is selected as the virtual tilt axis via the input 1420, such that the x-ray image 1402 may be tilted about the vertical virtual tilt axis 1527. It should be appreciated that the graphical user interface 1500 displays the vertical virtual tilt axis 1527 over the x-ray image 1402 rather than the horizontal virtual tilt axis 1423, as the vertical or y-axis is selected as the virtual tilt axis.

Further, as depicted, a user 1580 presses the x-ray image 1402 at an input position to indicate a direction that the user 1580 desires to tilt the x-ray image 1402 about the vertical virtual tilt axis 1527. As the user 1580 is pressing the x-ray image 1402 to the right of the vertical virtual tilt axis 1527, the x-ray image 1402 is virtually tilted or rotated counter-clockwise about the vertical virtual tilt axis 1527. In contrast, if the user 1580 were pressing the x-ray image 1402 to the left of the vertical virtual tilt axis 1527, the x-ray image 1402 would instead be virtually tilted or rotated clockwise about the vertical virtual tilt axis 1527.

In some examples, the rotation rate of the x-ray image 1402 about a virtual tilt axis such as the vertical virtual tilt axis 1527 responsive to a user pressing the x-ray image 1402 at the input position may depend on one or more of the distance of the input position from to the vertical virtual tilt axis 1527 and the amount of pressure applied by the user 1580 at the input position. For example, the x-ray image 1402 may rotate about the vertical virtual tilt axis 1527 at a higher rotation rate for an input position closer to the vertical virtual tilt axis 1527 than for an input position further away from the vertical virtual tilt axis 1527. Additionally or alternatively, the x-ray image 1402 may rotate about the vertical virtual tilt axis 1527 at a rotation rate that increases with an increasing pressure applied by the user 1580 to the touchscreen. In some examples, a visual indication 1585 of the pressure or rotation rate is displayed on the x-ray image 1402 at the input position, wherein additional concentric circles are displayed for more pressure and fewer concentric circles are displayed for less pressure. In this way, the rotation rate of the tilting may be visualized.

Further, the x-ray image may be tilted in discrete steps or continuously based on an amount of time that the user 1580 is pressing the x-ray image 1402. For example, a single tap of the x-ray image 1402 may tilt the image in small steps, such as by 0.5 to 1 degree, whereas pressing and holding the x-ray image 1402 may continuously tilt the image continuously.

In examples wherein the rotation rate of the x-ray image 1402 about the vertical virtual tilt axis 1527 or the horizontal virtual tilt axis 1426 is adjustable according to the input pressure and/or the input position of the user 1580, the rotation rate may further be configured to decrease towards zero rotation as the tilting or rotation of the x-ray image 1402 approaches a maximum tilt. In other words, the virtual tilting of the x-ray image 1402 around the virtual tilt axis slows down as the virtual tilting reaches a maximum tilt.

Figure 16:
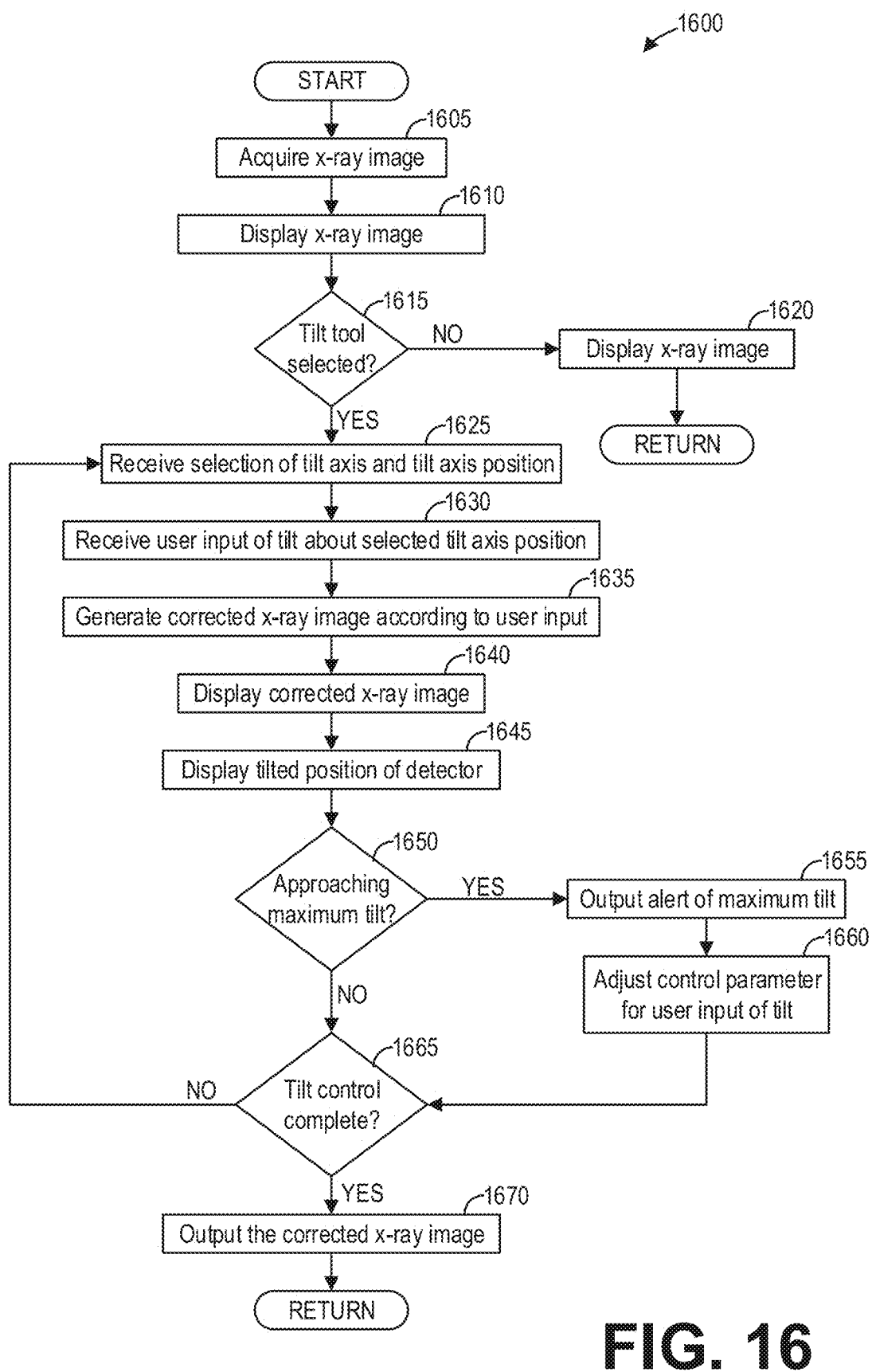
FIG. 16 shows a high-level flow chart illustrating an example method for correcting detector tilt based on user input according to an embodiment.

FIG. 16 shows a high-level flow chart illustrating an example method 1600 for correcting detector tilt based on user input according to an embodiment. In particular, method 1600 relates to applying a tilt correction to an x-ray image based on user input. Method 1600 is described with regard to the systems and components of FIGS. 1, 14, and 15, though it should be appreciated that method 1600 may be implemented with other systems and components without departing from the scope of the present disclosure. Method 1600 may be implemented as executable instructions in non-transitory memory, such as memory 182, and may be executed by one or more processors, such as processor 181, image processor 192, and detector tilt correction unit 193 of an x-ray imaging system such as the x-ray imaging system 100.

Method 1600 begins at 1605. At 1605, method 1600 acquires an x-ray image of an imaging subject or an object 110. To that end, the object 110, which may comprise a region of interest 110 of the subject 112, is positioned between the x-ray source 104 and the x-ray detector 108. With the subject 112 positioned between the x-ray source 104 and the x-ray detector 108, method 1600 controls the x-ray controller 187 to drive the x-ray source 104 to generate an x-ray beam 106 towards the object 110. X-rays of the x-ray beam 106 attenuated by the object 110 are then detected by the x-ray detector 108, and the x-ray image corresponding to the detected x-rays are recorded by the x-ray data acquisition unit 191. In some examples, a plurality of markers or an anti-scatter grid may be provided between the object 110 and the x-ray detector 108 as described hereinabove.

At 1610, method 1600 displays the x-ray image acquired at 1605, for example via the display device 195. As an example, method 1600 further displays a graphical user interface, such as the graphical user interface 1400 described hereinabove, via the display device 195 with the x-ray image included therein. Further, as mentioned hereinabove, the display device 195 may comprise a touch-sensitive display device or touchscreen.

At 1615, method 1600 determines if a tilt tool, such as the virtual tilt tool 1410, is selected. If the tilt tool is not selected ("NO"), method 1600 continues to 1620. At 1620, method 1600 continues displaying the x-ray image. Method 1600 then returns.

However, referring again to 1615, if the tilt tool is selected ("YES"), method 1600 proceeds to 1625. At 1625, method 1600 receives a selection of a tilt axis and a tilt axis position. Method 1600 may receive the selection of the tilt axis and/or the tilt axis position via one or more of the user interface 183 and the display device 195, for example by interacting with the input 1420 or with one of the input sliders 1422 and 1426. In some examples, one or more of a default tilt axis and a default tilt axis position may be automatically selected. For example, the user may select a tilt axis without specifying a tilt axis position, and so the default tilt axis position may be automatically selected. As an illustrative example, the default tilt axis may comprise the horizontal or x-axis while the default tilt axis position may comprise a tilt axis centered in the image.

At 1630, method 1600 receives user input of tilt about the selected tilt axis position. Method 1600 may receive the user input of the tilt about the selected tilt axis at the selected tilt axis position via one or more of the user interface 183 and the display device 195. For example, the user may interact with the input 1430 to adjust the tilt, for example by controlling a keyboard or mouse of the user interface 183 or by interacting with the display device 195. As another example, the user may click, with a device of the user interface 183, or press, with a finger or stylus applied to the display device 195, a position of the x-ray image displayed on the display device 195 to input an amount of tilt.

At 1635, method 1600 generates a corrected x-ray image according to the user input. For example, method 1600 transforms the pixels of the x-ray image via a rotation matrix as described hereinabove, with the tilt angle input by the user at 1630 as the rotation angle in the rotation matrix. At 1640, method 1600 displays the corrected x-ray image via the display device 195.

Further, at 1645, method 1600 displays a tilted position of the detector according to the tilt angle input by the user. For example, method 1600 may update the visual output 1450 according to the tilt angle input by the user. In this way, the user may verify and understand the relation of the plane of the corrected x-ray image to the detector plane, to ensure that the x-ray image is being correctly tilted. Further, the visual output 1450 of the tilted position of the x-ray detector informs the user of how to adjust the physical orientation of the x-ray detector such that the tilt correction may be unnecessary for subsequent image acquisitions with the x-ray detector.

At 1650, method 1600 determines if the tilt is approaching a maximum tilt. The maximum tilt comprises a maximum tilt angle that may be applied to the x-ray image data to achieve a threshold image quality. For example, as described hereinabove, interpolation may be used to generate corrected image pixels after rotation. Limits to the amount of tilt, corresponding to the maximum tilt, may be implemented such that image quality of the rotated image is not degraded beyond the threshold image quality after interpolation. Additionally or alternatively, predetermined thresholds for virtually tilting the x-ray image may be implemented based on the geometry of the x-ray detector rather than directly on the resulting image quality. For example, the maximum tilt may comprise 15 degrees if the tilt axis position is centered in the x-ray image, while the maximum tilt may comprise 5 degrees if the tilt axis position is closer to the edge of the x-ray image, as illustrative and non-limiting examples.

If the tilt input by the user is approaching the maximum tilt ("YES"), method 1600 continues to 1655. At 1655, method 1600 outputs an alert of the maximum tilt. At 1660, method 1600 adjusts a control parameter for user input of tilt. For example, method 1600 may decrease the rotation rate for the user input of tilt, such that pressing the x-ray image to further tilt the x-ray image tilts the image more slowly. Method 1600 then continues to 1665.

Referring again to 1650, if the tilt is not approaching the maximum tilt ("NO"), method 1600 proceeds to 1665. At 1665, method 1600 determines if the tilt control is complete. Tilt control may be complete once the user finalizes or confirms the virtual tilt applied to the x-ray image, for example via the input 1460 of the graphical user interface. If the tilt control is not complete ("NO"), method 1600 returns to 1625. Thus, until tilt control is complete, method 1600 continues to generate and display corrected x-ray images according to user input of tilt as well as selections of the tilt axis and the tilt axis position.

Once tilt control is complete ("YES"), method 1600 proceeds to 1670. At 1670, method 1600 outputs the corrected x-ray image via the display device 195. Method 1600 then returns.

A technical effect of the disclosure includes virtually rotating an x-ray image based on one or more tilt angles. Another technical effect of the disclosure includes the acquisition of an x-ray image with one or more shadows therein, and the rotation of the x-ray image according to the shape and/or size of the shadows. Yet another technical effect of the disclosure includes the display of a corrected x-ray image acquired with an x-ray detector tilted at an angle relative to an x-ray source, wherein the corrected x-ray image is rotated according to the angle. Another technical effect of the disclosure includes the real-time updated display of an x-ray image with rotations applied to the x-ray image by a user.

In one embodiment, a method comprises acquiring, with an x-ray detector tilted at an angle with respect to an x-ray source, an x-ray image, calculating the angle from the x-ray image, generating a corrected x-ray image based on the calculated angle, and displaying the corrected x-ray image.

In a first example of the method, the x-ray detector is configured with a plurality of markers positioned at a detecting surface of the x-ray detector, and calculating the angle from the x-ray image comprises measuring positions of a plurality of shadows in the x-ray image caused by the plurality of markers. In a second example of the method optionally including the first example, calculating the angle from the x-ray image further comprises calculating expected positions of the plurality of shadows according to a distance between the x-ray source and the x-ray detector. In a third example of the method optionally including one or more of the first and second examples, calculating the angle from the x-ray image further comprises measuring deviations of the measured positions of the plurality of shadows from the expected positions of the plurality of shadows. In a fourth example of the method optionally including one or more of the first through third examples, an anti-scatter grid is positioned adjacent to the x-ray detector during the acquisition of the x-ray image, and calculating the angle from the x-ray image comprises measuring shifts in a shadow of the anti-scatter grid in the x-ray image. In a fifth example of the method optionally including one or more of the first through fourth examples, the method further comprises applying a Fourier transform to the x-ray image and determining a grid frequency of the shadow of the anti-scatter grid. In a sixth example of the method optionally including one or more of the first through fifth examples, measuring shifts in the shadow of the anti-scatter grid in the x-ray image comprises comparing the grid frequency to a known grid frequency of the anti-scatter grid for an absence of detector tilt. In a seventh example of the method optionally including one or more of the first through sixth examples, generating the corrected x-ray image based on the calculated angle comprises rotating pixels of the x-ray image data in a detector plane to a corrected detector plane based on the calculated angle. In an eighth example of the method optionally including one or more of the first through seventh examples, generating the corrected x-ray image based on the calculated angle further comprises interpolating the rotated pixels in the corrected detector plane to obtain corrected pixels, wherein the corrected x-ray image comprises the corrected pixels. In a ninth example of the method optionally including one or more of the first through eighth examples, the method further comprises displaying the x-ray image, receiving input of the angle from a user, and generating the corrected x-ray image based on the angle input by the user.

In another embodiment, a method comprises acquiring, with an x-ray detector tilted at an angle with respect to an x-ray source, an x-ray image, automatically determining the angle from the x-ray image, receiving adjustments to the angle from a user, generating a corrected x-ray image based on the angle and the adjustments to the angle, and displaying the corrected x-ray image.

In a first example of the method, automatically determining the angle from the x-ray image comprises measuring shadows in the x-ray image cast by one of an anti-scatter grid or a plurality of markers positioned at a detecting surface of the x-ray detector. In a second example of the method optionally including the first example, receiving the adjustments to the angle from the user comprises displaying a first corrected x-ray image to the user in a graphical user interface, the first corrected x-ray image generated by rotating image pixels of the x-ray image according to the angle, receiving, from the user, a selection of a tilt axis and a tilt axis position relative to the x-ray image, and receiving, from the user, a selection of a tilt angle for rotating the first corrected x-ray image about the tilt axis at the tilt axis position, wherein the adjustments to the angle comprises the selection of the tilt angle around the tilt axis at the tilt axis position. In a third example of the method optionally including one or more of the first and second examples, generating the corrected x-ray image based on the angle and the adjustments to the angle comprises generating the corrected x-ray image by rotating image pixels of the first corrected x-ray image according to the selection of the tilt angle around the tilt axis at the tilt axis position. In a fourth example of the method optionally including one or more of the first through third examples, receiving the selection of the tilt angle comprises receiving, via a touch-sensitive display device, a touch input by the user at a position of the x-ray image. In a fifth example of the method optionally including one or more of the first through fourth examples, receiving the selection of the tilt angle further comprises measuring a pressure of the touch input to determine a rotation rate of the x-ray image about the tilt axis.

In yet another embodiment, an x-ray imaging system comprises an x-ray source for generating x-rays, an x-ray detector configured to detect the x-rays, and a processor configured with instructions in non-transitory memory that when executed cause the processor to: acquire, via the x-ray detector, an x-ray image; determine, from the x-ray image, a tilt angle of the x-ray detector relative to the x-ray source; generate a corrected x-ray image according to the tilt angle; and output, via a display device communicatively coupled to the processor, the corrected x-ray image.

In a first example of the system, the system further comprises a plurality of markers positioned at a detecting surface of the x-ray detector, and the processor is configured to determine the tilt angle by measuring a position of a plurality of shadows in the x-ray image caused by the plurality of markers. In a second example of the system optionally including the first example, the system further comprises an anti-scatter grid positioned adjacent to the x-ray detector for shielding the x-ray detector from scattered x-rays, and the processor is configured to determine the tilt angle by measuring shifts in a grid pattern in the x-ray image caused by the anti-scatter grid. In a third example of the system optionally including one or more of the first and second examples, the processor is further configured to display, via the display device, a graphical user interface including the x-ray image, receive, via a user interface or the display device, a selection of a second tilt angle about a selected tilt axis at a selected tilt axis position, and output, via the display device, a second corrected x-ray image generated according to the second tilt angle.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   acquiring, with an x-ray detector tilted at an angle with respect to an x-ray source, an x-ray image;
   measuring positions of shadows in the x-ray image;
   calculating the angle from the positions of the shadows in the x-ray image;
   generating a corrected x-ray image based on the calculated angle; and
   displaying the corrected x-ray image.

2. The method of claim 1, wherein the x-ray detector is configured with a plurality of markers positioned at a detecting surface of the x-ray detector, wherein measuring the positions of the shadows in the x-ray image comprises measuring positions of a plurality of shadows in the x-ray image caused by the plurality of markers.

3. The method of claim 2, wherein calculating the angle from the x-ray image further comprises:
   calculating expected positions of the plurality of shadows according to a distance between the x-ray source and the x-ray detector.

4. The method of claim 3, wherein calculating the angle from the x-ray image further comprises:

measuring deviations of the measured positions of the plurality of shadows in the x-ray image from the expected positions of the plurality of shadows.

5. The method of claim 1, wherein an anti-scatter grid is positioned adjacent to the x-ray detector during an acquisition of the x-ray image, wherein measuring the positions of the shadows in the x-ray image comprises:
measuring shifts in a shadow of the anti-scatter grid in the x-ray image.

6. The method of claim 5, further comprising:
applying a Fourier transform to the x-ray image and determining a grid frequency of the shadow of the anti-scatter grid.

7. The method of claim 6, wherein measuring shifts in the shadow of the anti-scatter grid in the x-ray image comprises:
comparing the grid frequency of the shadow of the anti-scatter grid to a known grid frequency of the anti-scatter grid for an x-ray detector not tilted with respect to an x-ray source.

8. The method of claim 1, wherein generating the corrected x-ray image based on the calculated angle comprises:
rotating pixels of the x-ray image in a detector plane to a corrected detector plane based on the calculated angle.

9. The method of claim 8, wherein generating the corrected x-ray image based on the calculated angle further comprises:
interpolating the rotated pixels in the corrected detector plane to obtain corrected pixels, wherein the corrected x-ray image comprises the corrected pixels.

10. The method of claim 1, further comprising:
displaying the x-ray image;
receiving an input of the angle from a user; and
generating the corrected x-ray image based on the angle input by the user.

11. A method, comprising:
acquiring, with an x-ray detector tilted at an angle with respect to an x-ray source, an x-ray image;
automatically determining the angle from the x-ray image;
receiving adjustments to the angle from a user;
generating a corrected x-ray image based on the angle and the adjustments to the angle; and
displaying the corrected x-ray image.

12. The method of claim 11, wherein automatically determining the angle from the x-ray image comprises:
measuring shadows in the x-ray image cast by one of an anti-scatter grid or a plurality of markers positioned at a detecting surface of the x-ray detector.

13. The method of claim 11, wherein receiving the adjustments to the angle from the user comprises:
generating a first corrected x-ray image by rotating image pixels of the x-ray image according to the angle;
displaying the first corrected x-ray image to the user in a graphical user interface;
receiving, from the user, a selection of a tilt axis and a tilt-axis position relative to the x-ray image; and
receiving, from the user, a selection of a tilt angle for rotating the first corrected x-ray image about the tilt axis at the tilt-axis position, wherein the adjustments to the angle comprises the selection of the tilt angle around the tilt axis at the tilt-axis position.

14. The method of claim 13, wherein generating the corrected x-ray image based on the angle and the adjustments to the angle comprises:
generating the corrected x-ray image by rotating image pixels of the first corrected x-ray image according to the selection of the tilt angle around the tilt axis at the tilt-axis position.

15. The method of claim 13, wherein receiving, from the user, the selection of the tilt angle comprises:
receiving, via a touch-sensitive display device, a touch input by the user at a position of the x-ray image.

16. The method of claim 15, wherein receiving, from the user, the selection of the tilt angle further comprises:
measuring a pressure of the touch input to determine a rotation rate of the x-ray image about the tilt axis.

17. An x-ray imaging system, comprising:
an x-ray source for generating x-rays;
an x-ray detector configured to detect the x-rays;
a display device; and
a processor configured with instructions in a non-transitory memory that when executed cause the processor to:
acquire, via the x-ray detector, an x-ray image;
measure a position of a shadow in the x-ray image;
determine, from the position of the shadow in the x-ray image, a tilt angle of the x-ray detector relative to the x-ray source;
generate a corrected x-ray image according to the tilt angle; and
output, via the display device communicatively coupled to the processor, the corrected x-ray image.

18. The system of claim 17, further comprising:
a plurality of markers positioned at a detecting surface of the x-ray detector,
wherein the processor is configured to measure the position of the shadow in the x-ray image by measuring positions of a plurality of shadows in the x-ray image caused by the plurality of markers.

19. The system of claim 17, further comprising:
an anti-scatter grid positioned adjacent to the x-ray detector for shielding the x-ray detector from scattered x-rays,
wherein the processor is configured to measure the position of the shadow in the x-ray image by measuring shifts in a grid pattern in the x-ray image caused by the anti-scatter grid.

20. The system of claim 17, wherein the processor is further configured to:
display, via the display device, a graphical user interface including the x-ray image;
receive, via a user interface or the display device, a selection of a second tilt angle about a selected tilt axis at a selected tilt-axis position; and
output, via the display device, a second corrected x-ray image generated according to the second tilt angle.

* * * * *